(12) United States Patent
Poznansky

(10) Patent No.: US 11,890,348 B2
(45) Date of Patent: Feb. 6, 2024

(54) LOCALIZED DELIVERY OF ANTI-FUGETACTIC AGENT FOR TREATMENT OF CANCER

(71) Applicant: THE GENERAL HOSPITAL CORPORATION, Boston, MA (US)

(72) Inventor: Mark C. Poznansky, Newton Center, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/760,772

(22) PCT Filed: Sep. 16, 2016

(86) PCT No.: PCT/US2016/052312
§ 371 (c)(1),
(2) Date: Mar. 16, 2018

(87) PCT Pub. No.: WO2017/049208
PCT Pub. Date: Mar. 23, 2017

(65) Prior Publication Data
US 2018/0256742 A1    Sep. 13, 2018

Related U.S. Application Data

(60) Provisional application No. 62/220,912, filed on Sep. 18, 2015.

(51) Int. Cl.
| | | |
|---|---|---|
| *A61K 47/68* | (2017.01) | |
| *A61K 39/39* | (2006.01) | |
| *A61K 39/395* | (2006.01) | |
| *A61P 35/00* | (2006.01) | |
| *A61K 39/00* | (2006.01) | |
| *C07K 16/30* | (2006.01) | |
| *C07K 14/52* | (2006.01) | |
| *A61K 31/395* | (2006.01) | |
| *A61K 45/06* | (2006.01) | |

(52) U.S. Cl.
CPC ........ *A61K 47/6803* (2017.08); *A61K 31/395* (2013.01); *A61K 39/39* (2013.01); *A61K 39/395* (2013.01); *A61K 45/06* (2013.01); *A61K 47/6851* (2017.08); *A61P 35/00* (2018.01); *C07K 14/52* (2013.01); *C07K 16/30* (2013.01); *A61K 39/00* (2013.01)

(58) Field of Classification Search
CPC ............ A61K 2121/00; A61K 2123/00; A61K 47/00; A61K 47/6803; A61K 39/00; A61K 39/39; A61K 39/395; A61K 47/6851; A61K 31/00; A61K 31/395; A61K 45/00; A61K 45/06; A61P 35/00; C07K 14/52; C07K 16/30
USPC ........ 424/1.11, 1.49, 1.65, 9.1, 9.2
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,075,109 A | 12/1991 | Tice |
| 5,272,082 A | 12/1993 | Santoli et al. |
| 5,514,555 A | 5/1996 | Springer et al. |
| 5,545,806 A | 8/1996 | Lonberg et al. |
| 5,545,807 A | 8/1996 | Surani et al. |
| 5,569,825 A | 10/1996 | Lonberg et al. |
| 5,583,131 A | 12/1996 | Bridger et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,858,358 A | 1/1999 | June et al. |
| 5,883,223 A | 3/1999 | Gray |
| 6,352,694 B1 | 3/2002 | June et al. |
| 6,448,054 B1 | 9/2002 | Poznansky et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,141,363 B2 * | 11/2006 | Poznansky ................ A61P 7/06 435/4 |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,618,817 B2 | 11/2009 | Campbell |
| 7,745,578 B2 * | 6/2010 | Poznansky ............. A61K 35/26 530/328 |
| 7,775,469 B2 * | 8/2010 | Poznansky ................ A61P 9/00 424/85.1 |
| 7,935,692 B2 | 5/2011 | Bridger et al. |
| 8,034,332 B2 | 10/2011 | Klingemann |
| 8,034,334 B2 | 10/2011 | Dudley et al. |
| 8,329,178 B2 * | 12/2012 | Marasco ............... C07K 16/005 424/133.1 |
| 8,383,099 B2 | 2/2013 | Dudley et al. |
| 8,906,682 B2 | 12/2014 | June et al. |

(Continued)

FOREIGN PATENT DOCUMENTS

| | | |
|---|---|---|
| CN | 103736092 | 4/2014 |
| MX | 2017013666 | 7/2018 |

(Continued)

OTHER PUBLICATIONS

Drugs.com (https://www.drugs.com/avastin.html, 5 pages) (Year: 2019).*

(Continued)

*Primary Examiner* — D. L. Jones
(74) *Attorney, Agent, or Firm* — Fish & Richardson P.C.

(57) ABSTRACT

The invention described herein relates to methods and compositions for treating cancer in a patient, or a tumor cell, by administering an effective amount of an antibody-antifugetactic agent complex.

16 Claims, 1 Drawing Sheet

(56) References Cited

U.S. PATENT DOCUMENTS

| | | |
|---|---|---|
| 2002/0068044 A1 | 6/2002 | Klingemann |
| 2005/0003508 A1 | 1/2005 | Abribat et al. |
| 2006/0121005 A1 | 6/2006 | Berenson et al. |
| 2008/0247990 A1 | 10/2008 | Campbell |
| 2008/0300165 A1 | 12/2008 | Poznansky et al. |
| 2012/0154861 A1 | 6/2012 | Sato |
| 2012/0321666 A1 | 12/2012 | Cooper et al. |
| 2014/0055415 A1 | 2/2014 | Kim |
| 2014/0065096 A1 | 3/2014 | Ichim et al. |
| 2014/0099714 A1 | 4/2014 | Klingemann |
| 2014/0219952 A1 | 8/2014 | Cameron |
| 2016/0057554 A1 | 2/2016 | Lavery et al. |

FOREIGN PATENT DOCUMENTS

| | | |
|---|---|---|
| WO | 2011068894 | 6/2011 |
| WO | 2013082254 | 6/2013 |
| WO | WO 2013/154760 | 10/2013 |
| WO | WO 2014/055668 | 4/2014 |
| WO | 2014191128 | 12/2014 |
| WO | WO 2015/019284 | 2/2015 |
| WO | 2016176154 | 11/2016 |

OTHER PUBLICATIONS

Notification of Transmittal of the International Search Report and the Written Opinion of the Searching Authority, or the Declaration corresponding to International Application No. PCT/US2016/052312 dated Dec. 28, 2016.

Notification Concerning Transmittal of International Preliminary Report, on Patentability corresponding to International Application No. PCT/US2016/052312 dated Mar. 29, 2018.

Bale et al., "Factors Influencing Localization of Labeled Antibodies in Tumors," *Cancer Research*, Aug. 1980, 40:2965-2972.

Bird et al., "Single-chain antigen-binding proteins," *Science*, Oct. 1988, 242(4877):423-426.

Boerner et al., "Production of antigen-specific human monoclonal antibodies from in vitro-primed human splenocytes," *J. Immunol.*, Jul. 1991, 147(1):86-95.

Debnath et al., "Small molecule inhibitors of CXCR4," *Theranostics*, 2013, 3(1):47-75.

DeWeger et al., "Eradication Of Murine Lymphoma And Melanoma Cells By Chlorambucil-Antibody Complexes," *Immunological Rev.*, Feb. 1982, 62(1):29-45.

Fishwild et al., "High-avidity human IgGk monoclonal antibodies from a novel strain of minilocus transgenic mice," *Nature Biotechnology*, Jul. 1996, 14(7):845-51.

Ghose and Blair., "Antibody-linked cytotoxic agents in the treatment of cancer: current status and future prospects," *J. Natl. Cancer Inst.*, Sep. 1978, 61(3):657-676.

Glienke et al., "Advantages and applications of CAR-expressing natural killer cells," *Frontiers in Pharmacol.*, Feb. 2015, 6:21, 7 pages.

Gregoriadis, "Targeting of drugs," *Nature*, 1977, 265(5593):407-441.

Gregoriadis, "Targeting of drugs: Possibilities in viral chemotherapy and prophylaxis," *Pharmac. Then.*, Jan. 1980, 10(1):103-118.

Heath et al., "Covalent attachment of immunoglobulins to liposomes via glycosphingolipids," *Biochim. Biophys. Acta.*, Jan. 1981, 640(1):66-81.

Hoogenboom & Winter, "By-passing immunisation: human antibodies from synthetic repertoires of germline VH gene segments rearranged in vitro," *J. Mo. Biol.*, Sep. 1992, 227(2):381-388.

Huang et al., "Monoclonal antibody covalently coupled with fatty acid. A reagent for in vitro liposome targeting," *J. Biol. Chem.*, Sep. 1980, 255(17):8015-8018.

Hunkapiller & Hood, "Immunology: the growing immunoglobulin gene superfamily," *Nature*, Sep. 1986, 323(6083):15-16.

Huston et al., "Protein engineering of antibody binding sites: recovery of specific activity in an anti-digoxin single-chain Fv analogue produced in Escherichia coli," *Proc. Natl. Acad. Sci. USA.*, Aug. 1988, 85(16):5879-5883.

Jansons and Mallet, "Targeted liposomes: a method for preparation and analysis," Anal. Biochem., Feb. 1981, 111(1):54-59.

Jones et al., "Replacing the complementarity-determining regions in a human antibody with those from a mouse," *Nature*, May 1986, 321(6069):522-525.

Karush et al., "Interaction of a bivalent ligand with IgM anti-lactose antibody," *Biochem.*, May 1979, 18(11):2226-2232.

Kohler & Milstein, "Continuous cultures of fused cells secreting antibody of predefined specificity," *Nature*, Aug. 1975, 256:495-497.

Kozbor et al., "The production of monoclonal antibodies from human lymphocytes," *Immunology Today*, Mar. 1983, 4(3):72-79.

Lanzavecchia et al., "The use of hybrid hybridomas to target human cytotoxic T lymphocytes," *Eur. J. Immunol.*, 1987, 17(1):105-111.

Leserman et al., "Targeting to cells of fluorescent liposomes covalently coupled with monoclonal antibody or protein A," Dec. 1980, *Nature*, 288(5791):602-604.

Lonberg & Huszar., "Human antibodies from transgenic mice," *Intern. Rev. Immunol.*, Jan. 1995, 13(1):65-93.

Lonberg et al., "Antigen-specific human antibodies from mice comprising four distinct genetic modifications," *Nature*, Apr. 1994, 368(6474):856-859.

Marks et al., "By-Passing Immunization: Building High Affinity Human Antibodies by Chain Shuffling," *Biotechnology*, Jul. 1992, 10:779-783.

Martin et al., "Immunospecific targeting of liposomes to cells: a novel and efficient method for covalent attachment of Fab' fragments via disulfide bonds," *Biochem.*, Jul. 1981, 20(14):4229-4238.

McCafferty et al., "Phage antibodies: filamentous phage displaying antibody variable domains," *Nature*, Dec. 1990, 348(6301):552-554.

Morrison, "Success in specification," *Nature*, Apr. 1994, 368(6474):812-813.

Neuberger, "Generating high-avidity human Mabs in mice," *Nature Biotechnology*, Jul. 1996, 14(7):826.

Presta, "Antibody engineering," *Curr. Op. Struct. Biol.*, Aug. 1992, 2(4):593-596.

Riechmann et al., "Reshaping human antibodies for therapy," *Nature*, Mar. 1988, 332(6162):323- 327.

Righi et al., "CXCL12/CXCR4 blockade induces multimodal antitumor effects that prolong survival in an immunocompetent mouse model of ovarian cancer," *Cancer Res.*, Aug. 2011, 71(16):5522-5534.

Rodriguez-Madoz et al., "Semliki forest virus vectors engineered to express higher IL-12 levels induce efficient elimination of murine colon adenocarcinomas," *Molecular Therapy*, Jul. 2005, 12(1):153-163.

Santini et al., "A controlled-release microchip," *Nature*, Jan. 1999, 397(6717):335-338.

Scott et al., "Monoclonal antibodies in cancer therapy," *Cancer Immunity*, Jan. 2012, 12(1):14.

Smith et al., "Localized expression of an anti-TNF single-chain antibody prevents development of collagen-induced arthritis," *Gene. Ther.*, Aug. 2003, 10(15):1248-1257.

Trouet et al., "DNA, liposomes, and proteins as carriers for antitumoral drugs," 1980, *Recent Results Cancer Res.*, 1980, 75:229-235.

Verhoeyen et al., "Reshaping human antibodies: grafting an antilysozyme activity," *Science*, Mar. 1988, 239(4847):1534-1536.

Vianello et al., "Murine B16 melanomas expressing high levels of the chemokine stromal-derived factor-1/CXCL12 induce tumor-specific T cell chemorepulsion and escape from immune control," *The Journal of Immunology*, Mar. 2006, 76(5):2902-2914.

Wang et al., "Universal PCR amplification of mouse immunoglobulin gene variable regions: the design of degenerate primers and an assessment of the effect of DNA polymerase 3' to 5' exonuclease activity," *J. Immunol. Methods*, Jan. 2000, 233(1-2):167-177.

Yeh et al., "Cell Surface Antigens Of Human Melanoma Identified By Monoclonal Antibody," *Proc. Natl. Acad. Sci.*, Jun. 1979, 76(6):2927-2931.

(56) References Cited

OTHER PUBLICATIONS

Liu et al., "CXCR4 antagonist AMD3 100 redistributes leukocytes from primary immune organs to secondary immune organs, lung, and blood in mice," Eur. J. Immunol., Jun. 2015, 45:1855-1867.
Nimmagadda et al., "Molecular Imaging of CXCR4 Receptor Expression in Human Cancer Xenografts with [64Cu]AMD3100 Positron Emission Tomography," Cancer Res., May 15, 2010, 70(10):3935-3944.
CN Office Action in Chinese Appln. No. 201680065811.7, dated May 8, 2021, 14 pages (with English translation).
JP Office Action in Japanese Appln. No. 2018-514872, dated Jun. 21, 2021, 10 pages (with English translation).
Lee et al., "Dynamic alterations in chemokine gradients induce transendothelial shuttling of human T cells under physiologic shear conditions," Journal of Leukocyte Biology, 2009, 86:1285-1294.
MX Office Action in Mexican Appln. No. MX/a/2018/003308, dated Oct. 19, 2021, 9 pages (with English translation).
Office Action in Mexican Appln. No. MX/a/2018/003308, dated Mar. 7, 2023, 21 pages (with English machine translation).

\* cited by examiner

LOCALIZED DELIVERY OF ANTI-FUGETACTIC AGENT FOR TREATMENT OF CANCER

CROSS REFERENCE TO RELATED APPLICATIONS

This application is a 35 U.S.C. § 371 national phase application of PCT Application PCT/US2016/052312 filed Sep. 16, 2016, which claims priority under 35 U.S.C. § 119(e) to U.S. Provisional Application No. 62/220,912, filed Sep. 18, 2015, the entire contents of each of which are incorporated herein by reference in its entirety.

BACKGROUND OF THE INVENTION

Cell movement in response to specific stimuli occurs in both prokaryotes and eukaryotes. Cell movement has been classified into three types: chemotaxis, or the movement of cells along a gradient towards an increasing concentration of a chemical; negative chemotaxis, which has been defined as the movement down a gradient of a chemical stimulus; and chemokinesis, or the increased random movement of cells induced by a chemical agent.

Chemotaxis and chemokinesis occur in mammalian cells in response to a class of proteins, called chemokines. Additionally, chemorepellent, or fugetactic, activity has been observed in mammalian cells. For example, some tumor cells secrete concentrations of chemokines that are sufficient to repel immune cells from the site of a tumor, thereby reducing the immune system's ability to target and eradicate the tumor. Metastasizing cancer cells may use a similar mechanism to evade the immune system.

Anti-fugetactic agents have been described that inhibit the fugetactic activity of tumor cells and allow the patient's immune system to target the tumor (see US 2008/0300165, incorporated herein by reference in its entirety). However, treatment with such agents alone may not be sufficient to eradicate a tumor in all patients, depending on the type of tumor, size of tumor, number of metastases, site(s) of metastasis, patient's health, etc.

There remains a need for treatments and compositions that target tumors to efficiently kill tumors and/or metastasizing cancer cells.

SUMMARY OF THE INVENTION

This invention relates to the treatment of a tumor with an antibody-anti-fugetactic agent complex.

One or more additional cancer therapies may optionally be administered, e.g. chemotherapy, radiotherapy, immunotherapy, and/or vaccine therapy. Immunotherapy (immunotherapy agent) includes, without limitation, any living immune cell that can be administered to a patient, and/or antibodies specific for a target cell (e.g., a tumor cell). Preferably, the immunotherapy agent is an NK cell or a T cell, or a modification or derivative thereof (e.g., a CAR T cell). In some embodiments, additional anti-cancer therapy is not administered at the same time as the treatment with the anti-fugetactic agent and the antibody.

Repulsion of tumor antigen-specific T-cells, e.g. from a tumor expressing high levels of CXCL12 or interleukin 8, allows the tumor cells to evade immune control. This invention is predicated on the discovery that treatment with an effective amount of antibody-anti-fugetactic agent complexes for a period of time sufficient to provide attenuate the fugetactic effect of the chemokine restores immune defenses against tumors, and also allows anti-cancer agents (e.g., chemotherapeutic agents, immunotherapeutic agents, radiotherapeutic agents, and the like) to better access the tumor in order to reduce or eradicate the tumor.

Without being bound by theory, it is believed that co-administration of an antibody-anti-fugetactic agent complex with an additional anti-cancer agent as described herein will lead to a synergistic response in a patient with a tumor, such that the patient has a better outcome than with either therapy alone. Anti-cancer agents include, without limitation, known cancer therapies, e.g. chemotherapy, radiotherapy, immunotherapy, and/or vaccine therapy. In preferred embodiments, the additional agent is vaccine therapy, cell therapy, antibody therapy, or a check-point inhibitor. Without being bound by theory, it is believed that such methods are especially beneficial, by way of non-limiting example, if the tumor is large in size, there are multiple tumors in the patient, the patient's immune system is compromised, etc.

As many as 85% of solid tumors and leukemias express CXCL12 at a level sufficient to have fugetactic effects, e.g. repulsion of immune cells from the tumor. Cancers that express CXCL12 at such levels include, but are not limited to, prostate cancer, lung cancer, breast cancer, pancreatic cancer, ovarian cancer, gastric cancer, esophageal cancer, glioma, and leukemia.

One aspect of the invention relates to a method for delivering an antibody-anti-fugetactic agent complex to a tumor expressing an amount of a chemokine sufficient to produce a fugetactic effect, which method comprises administering to the tumor an effective amount of an antibody-anti-fugetactic agent complex for a sufficient period of time so as to inhibit said fugetactic effect. In one embodiment, more than one antibody-anti-fugetactic agent complex is administered, wherein the antibody of each complex has specificity to the same or a different tumor antigen.

In some embodiments, the chemokine is CXCL12 or interleukin 8. In some embodiments, the tumor is a solid tumor. In some embodiments, the anti-fugetactic agent is AMD3100 or derivative thereof, KRH-1636, T-20, T-22, T-140, TE-14011, T-14012, TN14003, TAK-779, AK602, SCH-351125, Tannic acid, NSC 651016, thalidomide, or GF 109230X.

In some embodiments, the method further comprising contacting said tumor with an anti-cancer agent. In some embodiments, the anti-cancer agent is s a chemotherapeutic agent, a radiotherapeutic agent, an immunotherapy agent, or an anti-cancer vaccine. In some embodiments, the anti-cancer agent is administered within three days of administering the antibody-anti-fugetactic agent complex. In some embodiments, the anti-cancer agent is administered the day after completion of administering the antibody-anti-fugetactic agent complex. In some embodiments, the anti-cancer agent is administered prior to administering the antibody-anti-fugetactic agent complex. In some embodiments, the anti-cancer agent is administered concurrently with the antibody-anti-fugetactic agent complex.

In some embodiments, the immunotherapy agent is a natural killer (NK) cell. In some embodiments, the NK cell is a modified NK cell, an autologous NK cell, or a NK cell line (e.g., NK-92). In some embodiments, the immunotherapy agent is a T cell. In some embodiments, the T cell is a modified T cell, a cell line, CAR-T (chimeric antigen receptor T cell), or a T-ALL cell.

One aspect of the invention relates to a method for delivering an antibody-anti-fugetactic agent complex to a tumor expressing an amount of a chemokine sufficient to produce a fugetactic effect, which method comprises administering to the tumor an effective amount of at least one antibody-anti-fugetactic agent complex for a sufficient period of time so as to inhibit said fugetactic effect, wherein the antibody has specificity for a tumor antigen.

One aspect of the invention relates to a method for treating a metastatic tumor in a patient in need thereof, which method comprises systemic administering to the patient an effective amount of at least one antibody-anti-fugetactic agent complex, followed by administering an effective amount of at least one antibody-anti-fugetactic agent complex for a sufficient period of time so as to inhibit a fugetactic effect produced by a chemokine that is expressed by the tumor, wherein the antibody has specificity for a tumor antigen.

In some embodiments, the method includes contacting said tumor with an anti-cancer agent. In some embodiments, the anti-cancer agent is selected from the group consisting of a chemotherapeutic agent, a radiotherapeutic agent, an immunotherapy agent, and an anti-cancer vaccine.

In some embodiments, the antibody-anti-fugetactic agent complex is administered subdermally, intra-arterially, or intravenously. In some embodiments, the immunotherapy agent is administered intravenously or directly into the tumor.

One aspect of the invention relates to a solid tumor cell expressing CXCL12 that has been contacted with an antibody-anti-fugetactic agent complex and an anti-cancer agent.

In some embodiments, the anti-fugetactic agent is AMD3100 or a derivative thereof, KRH-1636, T-20, T-22, T-140, TE-14011, T-14012, TN14003, TAK-779, AK602, SCH-351125, Tannic acid, NSC 651016, thalidomide, or GF 109230X.

One aspect of the invention relates to a method for delivering a composition to a tumor expressing an amount of a chemokine sufficient to produce a fugetactic effect, which method comprises administering to the tumor an effective amount of the composition for a sufficient period of time so as to inhibit said fugetactic effect, wherein the composition comprises an antibody having specificity to a tumor antigen, an anti-fugetactic agent, and an immunotherapeutic agent, wherein the anti-fugetactic agent is associated with the immunotherapeutic agent. For example, the immunotherapy agent may comprise immune cells having the anti-fugetactic agent bound to receptors on the cell surface. In preferred embodiments, the receptors include CXCR4.

One aspect of the invention relates to a method for delivering a composition to a tumor expressing an amount of a chemokine sufficient to produce a fugetactic effect, which method comprises administering to the tumor an effective amount of the composition comprising an ex vivo autologous T cell population obtained from a mammalian patient having a cancerous tumor said population having varying concentrations of an antibody-anti-fugetactic agent complex bound to individual T cells through a receptor, wherein said population exhibits overall anti-fugetactic properties in vivo relative to said cancerous tumor. In one embodiment, the receptor is CXCR4. In one embodiment, the T cells express a chimeric antigen receptor.

One aspect of the invention relates to a kit of parts comprising a first container comprising an antibody-anti-fugetactic agent complex and a second container comprising an anti-cancer agent.

One aspect of the invention relates to a kit of parts comprising a first container comprising an anti-fugetactic agent-immunotherapy agent complex and a second container comprising an antibody.

In some embodiments, the anti-fugetactic agent is AMD3100 or a derivative thereof, KRH-1636, T-20, T-22, T-140, TE-14011, T-14012, TN14003, TAK-779, AK602, SCH-351125, Tannic acid, NSC 651016, thalidomide, or GF 109230X.

In some embodiments, the antibody has specificity to an antigen expressed by the tumor to be targeted/treated.

One aspect of the invention relates to a method for treating cancer in a patient in need thereof, the method comprising administering to the patient an antibody-anti-fugetactic agent complex. Optionally, the patient is administered at least one additional anti-cancer agent.

One aspect of the invention relates to a method for increasing migration of immune cells to a tumor site in a patient having a cancer, the method comprising administering to the patient an antibody-anti-fugetactic agent complex. In one embodiment, the method increases migration of the patient's own immune cells to the tumor site. Optionally, the patient is administered at least one additional anti-cancer agent. In one embodiment, the method increases migration of the anti-cancer agent to the tumor site.

One embodiment of the invention relates to a method for inhibiting tumor cell metastasis in a patient in need thereof, the method comprising administering to the patient an antibody-anti-fugetactic agent complex. Optionally, the patient is administered at least one additional anti-cancer agent.

One embodiment of the invention relates to a method for locally treating a solid tumor in a mammal, the method comprising administering to the patient an antibody-anti-fugetactic agent complex. Optionally, the patient is administered at least one additional anti-cancer agent.

One embodiment of the invention relates to a method for killing a cancer cell, the method comprising administering to the patient an antibody-anti-fugetactic agent. Optionally, the patient is administered at least one additional anti-cancer agent.

In a preferred embodiment, the cancer, tumor, or cell expresses an amount of a chemokine sufficient to produce a fugetactic effect. In one embodiment, the chemokine is secreted by the cell or tumor, such that the fugetactic effect is present in the tumor microenvironment. In one embodiment, the concentration of the chemokine in the tumor microenvironment is greater than about 100 nM prior to treatment with the antibody-anti-fugetactic agent complex. In one embodiment, the chemokine is CXCL12 or IL-8. In a preferred embodiment, the chemokine is CXCL12.

In one embodiment, the tumor is a solid tumor. In one embodiment, the tumor is a non-solid tumor. In one embodiment, the tumor is a leukemia.

In one embodiment, the at least one additional anti-cancer agent is a chemotherapeutic agent, a radiotherapy agent, an immunotherapy agent, and/or an anti-cancer vaccine.

Without being bound by theory, it is believed that the therapy as described herein will allow the targeting of a tumor by the patient's own immune cells, and optionally by the additional anti-cancer agent. For example, the patient's immune system can be used to target a tumor or metastatic tumor cells in combination with an immunotherapy agent. In one embodiment, reducing the fugetactic activity of a tumor prevents the chemorepellant action of a tumor from inhibiting efficient targeting by immunotherapy agents (e.g., NK cells or T cells). In one embodiment, the patient is immunocompromised.

The anti-fugetactic agent may be any such agent known in the art. In one embodiment, the anti-fugetactic agent is an anti-fugetactic agent as described in U.S. Patent Application Publication No. 2008/0300165, which is hereby incorporated by reference in its entirety. In a preferred embodiment, the anti-fugetactic agent is AMD3100 (mozobil/plerixafor) or a derivative thereof, KRH-1636, T-20, T-22. T-140, TE-14011, T-14012, TN14003. TAK-779, AK602, SCH-351125, Tannic acid, NSC 651016, thalidomide, GF 109230X, an antibody that interferes with dimerization of a fugetactic chemokine, or an antibody that interferes with dimerization of the receptor for a fugetactic chemokine. For example, the antibody may inhibit dimerization of CXCL12, IL-8, CXCR3, or CXCR4. In one embodiment, the anti-fugetactic agent is an antibody that interferes with binding of the chemokine to its receptor. In one embodiment, the anti-fugetactic agent is an antibody or lectin that binds CXCL12 or that binds to CXCR4 and blocks signaling therefrom. In a preferred embodiment, the anti-fugetactic agent is AMD3100.

In one embodiment, the immunotherapy agent is an NK cell. In one embodiment, the NK cell is an autologous NK cell. In one embodiment, the NK cell is a non-autologous NK cell. In one embodiment, the NK cell is a modified NK cell. In a preferred embodiment, the NK cell is a human NK cell.

In one embodiment, the immunotherapy agent is an NK cell line. In one embodiment, the immunotherapy agent is a modified NK cell line. In one embodiment, the NK cell line is NK-92. In one embodiment, the modified NK cell line is administered with an antibody specific for the tumor to be treated. In one embodiment, the NK cell line is administered with a cytokine (e.g., IL-2).

In one embodiment, the immunotherapy agent is a T cell. In one embodiment, the T cell is an autologous T cell. In one embodiment, the T cell is a non-autologous T cell. In one embodiment, the T cell is a modified T cell. In one embodiment, the T cell is a T cell line. In a preferred embodiment, the T cell is a human T cell or human T cell line.

The antibody-anti-fugetactic agent is optionally administered in combination with an anti-cancer agent. "In combination" refers to any combination, including sequential or simultaneous administration. In a preferred embodiment, the antibody-anti-fugetactic agent complex is administered separately from the anti-cancer agent. In one embodiment, the antibody-anti-fugetactic agent complex is administered in a single composition with the anti-cancer agent.

In one embodiment, the anti-cancer agent is administered intravenously.

In one embodiment, the antibody-anti-fugetactic agent complex is administered intravenously, subcutaneously, orally, or intraperitoneally. In a preferred embodiment, the antibody-anti-fugetactic agent complex is administered proximal to (e.g., near or within the same body cavity as) the tumor. In one embodiment, the antibody-anti-fugetactic agent complex is administered directly into the tumor or into a blood vessel feeding the tumor. In one embodiment, the antibody-anti-fugetactic agent complex is administered systemically. In a further embodiment, the antibody-anti-fugetactic agent complex is administered by microcatheter, or an implanted device, and an implanted dosage form.

In one embodiment, the antibody-anti-fugetactic agent complex is administered in a continuous manner for a defined period. In another embodiment, the antibody-anti-fugetactic agent complex is administered in a pulsatile manner. For example, the antibody-anti-fugetactic agent complex may be administered intermittently over a period of time.

In one embodiment, at least one additional anti-cancer agent is administered in combination with the antibody-anti-fugetactic agent complex and the immunotherapy agent. The anti-cancer agent(s) may be administered in any order, sequentially or concurrently, with the antibody-anti-fugetactic agent complex. In a preferred embodiment, the antibody-anti-fugetactic agent complex and the anti-cancer agent(s) are administered sequentially. In an especially preferred embodiment, the antibody-anti-fugetactic agent complex is administered prior to administration of the anti-cancer agent.

In a preferred embodiment, the antibody-anti-fugetactic agent complex and anti-cancer agent are administered sequentially. For example, the antibody-anti-fugetactic agent complex may be administered for a period of time sufficient to reduce or attenuate the fugetactic effect of the tumor, e.g. such that the antibody-anti-fugetactic agent complex has an anti-fugetactic effect; the anti-cancer agent can then be administered for a period of time during which the fugetactic effect of the tumor is reduced or attenuated. In one embodiment, the antibody-anti-fugetactic agent complex and anti-cancer agent are administered sequentially in an alternating manner at least until the condition of the patient improves. Improvement of the condition of the patient includes, without limitation, reduction in tumor size, a reduction in at least one symptom of the cancer, elimination of the tumor and/or metastases thereof, increased survival of the patient, and the like.

Without being bound by theory, it is believed that the antibody-anti-fugetactic agent complex will reduce the fugetactic effect of the chemokine-secreting tumor or cancer cell so as to allow better access to the tumor or cell by additional agents and immune cells. The anti-cancer agent(s) may be subsequently administered, e.g. during a period of time during which the fugetactic effect of the tumor or cell is reduced. It is further contemplated that administration of some anti-cancer agents will be more effective against a tumor after the tumor has been reduced in size. Accordingly, in a preferred embodiment, an antibody-anti-fugetactic agent complex is administered first, in an amount and for a period of time sufficient to provide a reduction in the fugetactic effect of the tumor; subsequent to the period of time of administration of the antibody-anti-fugetactic agent complex, an anti-cancer agent is administered, in an amount and for a period of time to provide a therapeutic effect against the tumor (e.g. reduction in tumor size, elimination or reduction of metastases, delay in tumor growth). In one embodiment, the antibody-anti-fugetactic agent complex is administered concurrently (e.g., separately or simultaneously) with an anti-cancer agent.

In a preferred embodiment, the sequential administration of the antibody-anti-fugetactic agent complex, anti-cancer agent and/or immunotherapy agent is repeated at least until the patient's condition improves. In one embodiment, the sequential administration of the agents is repeated until the tumor is eradicated.

In one embodiment, the antibody-anti-fugetactic agent complex and/or the anti-cancer agent are administered directly to the tumor site. In one embodiment, the antibody-anti-fugetactic agent complex and/or the anti-cancer agent are administered by direct injection into the tumor. In one embodiment, the antibody-anti-fugetactic agent complex and/or the anti-cancer agent are administered proximal to the tumor site. In a preferred embodiment, the antibody-anti-fugetactic agent complex and/or the anti-cancer agent are administered directly into a blood vessel associated with the tumor (e.g., via microcatheter injection into the blood vessels in, near, or feeding into the tumor).

This invention further relates to a kit of parts for treating cancer in a patient, the kit of parts comprising an effective amount of the antibody-anti-fugetactic agent complex and optionally an anti-cancer agent as described herein. Optionally, the kit comprises instructions for dosing of the antibody-anti-fugetactic agent complex and/or the anti-cancer agent.

This invention further relates to a tumor cell from a chemokine-expressing tumor, said cell having been contacted with an antibody-anti-fugetactic agent complex and optionally an anti-cancer agent. In one embodiment, the chemokine is CXCL12. In one embodiment, the chemokine is IL-8.

DETAILED DESCRIPTION

Figure 1:
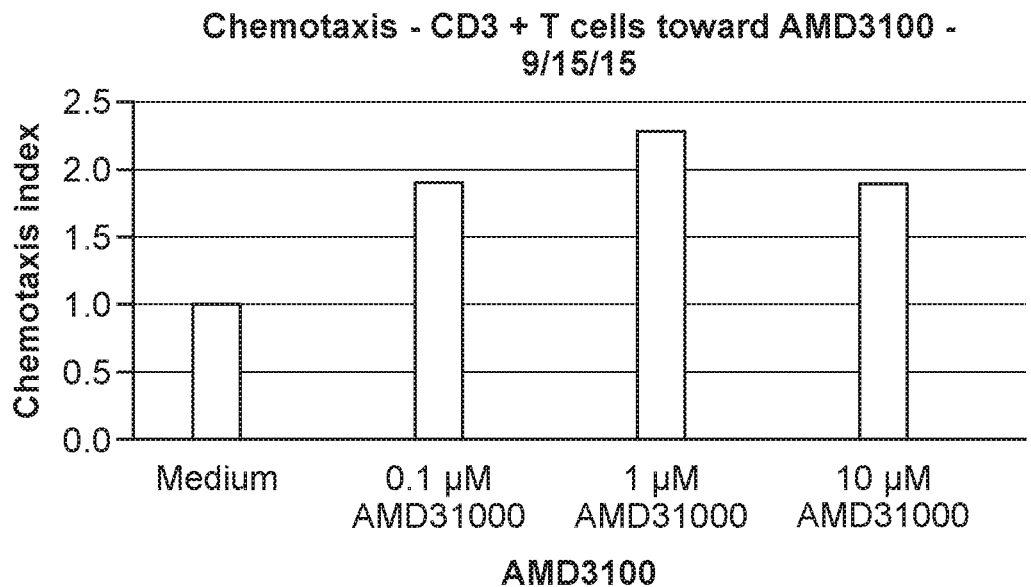
FIG. 1 demonstrates that AMD3100 has a bimodal effect on human T cell chemotaxis.

After reading this description, it will become apparent to one skilled in the art how to implement the invention in various alternative embodiments and alternative applications. However, not all embodiments of the present invention are described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Definitions

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

All numerical designations, e.g., pH, temperature, time, concentration, amounts, and molecular weight, including ranges, are approximations which are varied (+) or (−) by 10%, 1%, or 0.1%, where appropriate. It is to be understood, although not always explicitly stated, that all numerical designations may be preceded by the term "about." It is also to be understood, although not always explicitly stated, that the reagents described herein are merely examples and that equivalents of such are known in the art.

"Optional" or "optionally" means that the subsequently described event or circumstance can or cannot occur, and that the description includes instances where the event or circumstance occurs and instances where it does not.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., *Eur. J. Immunol.* 17, 105 (1987)) and single chains (e.g., Huston et al., *Proc. Natl. Acad. Sci. U.S.A.,* 85, 5879-5883 (1988) and Bird et al., *Science* 242, 423-426 (1988), which are incorporated herein by reference). (See, generally, Hood et al., *Immunology*, Benjamin, N.Y., 2ND ed. (1984); Harlow and Lane, *Antibodies. A Laboratory Manual*, Cold Spring Harbor Laboratory (1988); Hunkapiller and Hood, *Nature,* 323, 15-16 (1986), which are incorporated herein by reference). The antibody may be of any type (e.g., IgG, IgA, IgM, IgE or IgD). Preferably, the antibody is IgG.

The term "chimeric antibody" refers to an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "comprising" or "comprises" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

The term "epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and usually more, e.g. at least 5 or 8-10 amino acids in a unique spatial conformation. Methods of determining spatial conformation of epitopes include, for example, x-ray crystallography and 2-dimensional nuclear magnetic resonance. See, e.g., "Epitope Mapping Protocols" in Morris (ed. 1996) Methods in Molecular Biology, Vol. 66.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In some embodiments, the mammal is a mouse, a rat, a guinea pig, a non-human primate, a dog, a cat, or a domesticated animal (e.g. horse, cow, pig, goat, sheep). In especially preferred embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disease or disorder; (iii) slowing progression of the disease or disorder; and/or (iv) inhibiting, relieving, or slowing progression of one or more symptoms of the disease or disorder. For example, treatment of a cancer or tumor includes, but is not limited to, reduction in size of the tumor, elimination of the tumor and/or metastases thereof, inhibition of metastasis of the tumor, remission of the cancer, reduction or elimination of at least one symptom of the cancer, and the like.

The term "tumor cell" refers to precancerous, cancerous, and normal cells in a tumor. In some embodiments, the tumor cell is autologous or endogenous. In an alternative embodiment, the modified tumor cell is allogeneic. The allogeneic tumor cell thus can be maintained in a cell line. In this instance, the tumor cell can be selected from the cell line, irradiated, and introduced to the patient. Non-limiting examples of solid tumors include: Adrenal Cancer, Anal Cancer, Bile Duct Cancer, Bladder Cancer, Bone Cancer, Brain/CNS Tumors, Breast Cancer (including inflammatory breast cancer), Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST). Gestational Trophoblastic Disease. Hodgkin Disease, Kaposi Sarcoma, Kidney Cancer, Laryngeal and Hypopharyngeal Cancer, Liver Cancer, Lung Cancer, Lung Cancer—Non-Small Cell, Lung Cancer—Small Cell, Lung Carcinoid Tumor, Lymphoma of the Skin, Malignant Mesothelioma, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma. Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

Non-limiting examples of non-solid tumors include: Leukemia, Leukemia—Acute Lymphocytic (ALL) in Adults, Leukemia—Acute Myeloid (AML), Leukemia—Chronic Lymphocytic (CLL), Leukemia—Chronic Myeloid (CML), Leukemia—Chronic Myelomonocytic (CMML) Lymphoma, Multiple Myeloma, and Myelodysplastic Syndrome.

The term "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well-sequestered from the immune system, proteins that are normally produced in extremely small quantities, proteins that are normally produced only in certain stages of development, or proteins whose structure is modified due to mutation. Non-limiting examples of tumor antigens include EGFR, Her2, EpCAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin $\alpha V\beta 3$, Integrin $\alpha 5\beta 1$, ERBB2, ERBB3, MET, IGF1R, EPHA3, TRAILR1, TRAILR2, RANKL, FAP, mesothelin, and Tenascin. In some embodiments, the antibody has specificity to a protein or a peptide that is overexpressed on a tumor cell as compared to a corresponding non-tumor cell.

The term "administering" or "administration" of an agent, drug, or a natural killer cell to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

It is also to be appreciated that the various modes of treatment or prevention of medical diseases and conditions as described are intended to mean "substantial," which includes total but also less than total treatment or prevention, and wherein some biologically or medically relevant result is achieved.

The term "separate" administration refers to an administration of at least two active ingredients at the same time or substantially the same time by different routes.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients; there is no simultaneous treatment in this instance.

The term "simultaneous" therapeutic use refers to the administration of at least two active ingredients by the same route and at the same time or at substantially the same time.

The term "therapeutic" as used herein means a treatment and/or prophylaxis. A therapeutic effect is obtained by suppression, remission, or eradication of a disease state.

The term "therapeutically effective amount" or "effective amount" refers to an amount of the agent that, when administered, is sufficient to cause the desired effect. For example, an effective amount of an antibody-anti-fugetactic agent complex may be an amount sufficient to have an anti-fugetactic effect on a cancer cell or tumor (e.g. to attenuate a fugetactic effect from the tumor or cancer cell). By way of further example, an effective amount of one or more immune cells may result in lysis of at least a portion of tumor cells. The therapeutically effective amount of the agent will vary depending on the tumor being treated and its severity as well as the age, weight, etc., of the patient to be treated. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

As used to describe the present invention, "natural killer (NK) cells" are cells of the immune system that kill target cells in the absence of a specific antigenic stimulus, and without restriction according to MHC class. NK cells include NK cell lines. e.g., NK-92. Target cells may be tumor cells or cells harboring viruses. NK cells are characterized by the presence of CD56 and the absence of CD3 surface markers.

The term "endogenous NK cells" is used to refer to NK cells derived from a donor (or the patient), as distinguished from an exogenous cell line. Endogenous NK cells are generally heterogeneous populations of cells within which NK cells have been enriched. Endogenous NK cells may be intended for autologous or allogeneic treatment of a patient.

As used herein, "T cells" are cells of the immune system that play a role in cell-mediated immunity. T cells express the T-cell receptor (TCR) on the cell surface. There are several subsets of T cells, each with a unique function. T cells include helper T cell, cytotoxic T cells, memory T cells, suppressor (regulatory) T cells, natural killer T cells, and gamma delta T cells. Any T cell is contemplated herein. In a preferred embodiment, the T cell is suitable for use in adoptive cell transfer (ACT). In one embodiment, the T cell is a tumor-infiltrating lymphocyte (TIL). T cells include T cell lines, e.g., T-ALL.

The term "kill" with respect to a cell/cell population is directed to include any type of manipulation that will lead to the death of that cell/cell population.

"Cytokine" is a generic term for non-antibody, soluble proteins which are released from one cell subpopulation and which act as intercellular mediators, for example, in the generation or regulation of an immune response. See Human Cytokines: Handbook for Basic & Clinical Research (Aggrawal, et al. eds., Blackwell Scientific, Boston, Mass. 1991) (which is hereby incorporated by reference in its entirety for all purposes).

"CXCR4/CXCL12 antagonist" refers to a compound that antagonizes CXCL12 binding to CXCR4 or otherwise reduces the fugetactic effect of CXCL12.

By "fugetactic activity" or "fugetactic effect" it is meant the ability of an agent to repel (or chemorepel) a eukaryotic cell with migratory capacity (i.e., a cell that can move away from a repellant stimulus), as well as the chemorepellant effect of a chemokine secreted by a cell, e.g. a tumor cell. Usually, the fugetactic effect is present in an area around the cell wherein the concentration of the chemokine is sufficient to provide the fugetactic effect. Some chemokines, including interleukin 8 and CXCL12, may exert fugetactic activity at high concentrations (e.g., over about 100 nM), whereas lower concentrations exhibit no fugetactic effect and may even be chemoattractant.

Accordingly, an agent with fugetactic activity is a "fugetactic agent." Such activity can be detected using any of a variety of systems well known in the art (see. e.g., U.S. Pat. No. 5,514,555 and U.S. Patent Application Pub. No. 2008/0300165, each of which is incorporated by reference herein in its entirety). A preferred system for use herein is described in U.S. Pat. No. 6,448,054, which is incorporated herein by reference in its entirety.

The term "anti-fugetactic effect" refers to the effect of the anti-fugetactic agent to attenuate or eliminate the fugetactic effect of the chemokine.

The term "anti-cancer therapy" as used herein refers to known cancer treatments, including chemotherapy and radiotherapy, as well as immunotherapy and vaccine therapy.

"Immune cells" as used herein are cells of hematopoietic origin that are involved in the specific recognition of antigens. Immune cells include antigen presenting cells (APCs), such as dendritic cells or macrophages, B cells, T cells, etc.

The term "immunotherapy" or "immunotherapeutic agents" refers to cells and other products (e.g. antibodies) derived from the immune system or that uses the immune system to fight a cancer. Non-limiting examples include NK cells, T cells, NK or T cell cell lines, other immune-derived cells, antibodies (e.g. tumor-specific antibodies), and immune system activators (e.g., cytokines).

Antibodies Against Tumor Antigens

One aspect of the invention relates to a method for delivering an antibody-anti-fugetactic agent complex to a tumor expressing an amount of a chemokine sufficient to produce a fugetactic effect, which method comprises administering to the tumor an effective amount of more than one antibody-anti-fugetactic agent complex for a sufficient period of time so as to inhibit said fugetactic effect, wherein the antibody of each complex has specificity to the same or a different tumor antigen.

One aspect of the invention relates to a method for delivering an antibody-anti-fugetactic agent complex to a tumor expressing an amount of a chemokine sufficient to produce a fugetactic effect, which method comprises administering to the tumor an effective amount of at least one antibody-anti-fugetactic agent complex for a sufficient period of time so as to inhibit said fugetactic effect, wherein the antibody has specificity for a tumor antigen.

One aspect of the invention relates to a method for treating a metastatic tumor in a patient in need thereof, which method comprises systemically administering to the patient an effective amount of at least one antibody-anti-fugetactic agent complex, followed by administering to the tumor an effective amount of at least one antibody-anti-fugetactic agent complex for a sufficient period of time so as to inhibit a fugetactic effect produced by a chemokine that is expressed by the tumor, wherein the antibody has specificity for a tumor antigen.

One aspect of the invention relates to a method for delivering a composition to a tumor expressing an amount of a chemokine sufficient to produce a fugetactic effect, which method comprises administering to the tumor an effective amount of the composition for a sufficient period of time so as to inhibit said fugetactic effect, wherein the composition comprises an antibody having specificity to a tumor antigen, an anti-fugetactic agent, and an immunotherapeutic agent, wherein the anti-fugetactic agent is associated with the immunotherapeutic agent.

In one embodiment, the antibody against tumor antigen is an anti-cancer antibody. Non-limiting examples include trastuzumab (Herceptin®), bevacizumab (Avastin®), cetuximab (Erbitux®), panitumumab (Vectibix®), ipilimumab (Yervoy®), rituximab (Rituxan®), alemtuzumab (Campath®), ofatumumab (Arzerra®), gemtuzumab ozogamicin (Mylotarg®), brentuximab vedotin (Adcetris®), 90Y-ibritumomab tiuxetan (Zevalin®), and 131I-tositumomab (Bexxar®).

Additional antibodies are provided in Table 1.

TABLE 1

Anti-cancer antibodies

| Proprietary name | Trade name | Target; Format | Indication first approved or reviewed |
| --- | --- | --- | --- |
| Necitumumab | (Pending) | EGFR; Human IgG1 | Non-small cell lung cancer |
| Nivolumab | Opdivo | PD1; Human IgG4 | Melanoma |
| Dinutuximab | (Pending) | GD2; Chimeric IgG1 | Neuroblastoma |

TABLE 1-continued

Anti-cancer antibodies

| Proprietary name | Trade name | Target; Format | Indication first approved or reviewed |
|---|---|---|---|
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Obinutuzumab | Gazyva | CD20; Humanized IgG1; Glycoengineered | Chronic lymphocytic leukemia |
| Ado-trastuzumab emtansine | Kadcyla | HER2; humanized IgG1; immunoconjugate | Breast cancer |
| Pertuzumab | Perjeta | HER2; humanized IgG1 | Breast Cancer |
| Brentuximab vedotin | Adcetris | CD30; Chimeric IgG1; immunoconjugate | Hodgkin lymphoma, systemic anaplastic large cell lymphoma |
| Ipilimumab | Yervoy | CTLA-4; Human IgG1 | Metastatic melanoma |
| Ofatumumab | Arzerra | CD20; Human IgG1 | Chronic lymphocytic leukemia |

In some embodiments, the antibody is an antibody fragment that recognizes an antigen of interest (e.g., a tumor antigen). Antibodies exist, e.g., as intact immunoglobulins or as a number of well-characterized fragments produced by digestion with various peptidases. Thus, e.g., pepsin digests an antibody below the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region, thereby converting the F(ab')2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al. (1990) Nature 348: 552-554).

For preparation of antibodies, e.g., recombinant, monoclonal, or polyclonal antibodies, many techniques known in the art can be used (see, e.g., Kohler & Milstein (1975) Nature 256:495-497; Kozbor, et al. (1983) Immunology Today 4:72; Cole, et al., pp. 77-96 in Monoclonal Antibodies and Cancer Therapy (1985); Coligan (1991) Current Protocols in Immunology; Harlow & Lane (1988) Antibodies: A Laboratory Manual; and Goding (1986) Monoclonal Antibodies: Principles and Practice (2d ed.). Techniques for the production of single chain antibodies (U.S. Pat. No. 4,946, 778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty, et al. (1990) Nature 348:552-554; Marks, et al. (1992) Biotechnology 10:779-783).

Once the target tumor antigen is determined, it is used to generate antibodies, e.g., for immunotherapy. The ability of a particular antibody to recognize the same epitope as another antibody is typically determined by the ability of one antibody to competitively inhibit binding of the second antibody to the antigen. Many of a number of competitive binding assays can be used to measure competition between two antibodies to the same antigen. Example assays include Biacore assay, sandwich ELISA, and the like.

Methods of preparing polyclonal antibodies are known to the skilled artisan (e.g., Coligan, supra; and Harlow & Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler & Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid, fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (pp. 59-103 in Goding (1986) Monoclonal Antibodies: Principles and Practice). Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities of the bispecific antibody is for a tumor antigen, the other one is for a different tumor antigen. In one embodiment, one of the binding specificities of the bispecific antibody is for a tumor antigen, the other one is for a protein expressed by an immunotherapy agent. In one embodiment, one of the binding specificities of the bispecific antibody is for a tumor antigen, the other one is for an anti-fugetactic agent.

In some embodiments, the antibodies to the tumor antigen are humanized antibodies (e.g., Xenerex Biosciences, Medarex, Inc., Abgenix, Inc., Protein Design Labs, Inc.) Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, selectivity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones, et al. (1986) Nature 321:522-525; Riechmann, et al. (1988) Nature 332:323-329; and Presta (1992) Curr. Op. Struct. Biol. 2:593-596). Humanization can be essentially performed following the method of Winter and co-workers (Jones, et al. (1986) Nature 321:522-525; Riechmann, et al. (1988) Nature 332:323-327; Verhoeyen, et al. (1988) Science 239:1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom & Winter (1991) J. Mol. Biol. 227:381; Marks, et al. (1991) J. Mol. Biol. 222:581). The techniques of Cole, et al. and Boemer, et al. are also available for the preparation of human monoclonal antibodies (p. 77 in Cole, et al. (1985) Monoclonal Antibodies and Cancer Therapy; and Boemer, et al. (1991) J. Immunol. 147(1):86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described. e.g., in U.S. Pat. Nos. 5,545,807; 5,545,806; 5,569,825; 5,625,126; 5,633,425; 5,661,016, and in the following scientific publications: Marks, et al. (1992) Bio/Technology 10:779-783; Lonberg, et al. (1994) Nature 368:856-859; Morrison (1994) Nature 368:812-13; Fishwild. et al. (1996) Nature Biotechnology 14:845-51: Neuberger (1996) Nature Biotechnology 14:826; and Lonberg & Huszar (1995) Intern. Rev. Immunol. 13:65-93.

In certain preferred embodiments, the antibody is an scFv molecule. scFv molecules may be produced for example, as described by Smith et al. Gene Ther. 2003 August; 10(15) 1248-57. Likewise, scFv antibodies may be produced as described by Wang et al., J Immunol Methods. 2000 233(1-2): 167-77, which is incorporated herein by reference in its entirety.

Systems capable of expressing antibodies in vivo are known in the art. By way of example and not limitation, the system can use the mediated antibody expression system disclosed in Fang et al., Nature Biotech. 23(5) 2005 and U.S. Patent Publication 2005/0003508, the disclosures of which are expressly incorporated by reference herein in their entirety. Other systems known in the art are contemplated, and can also be adapted to produce antibodies in vive as described herein.

Antibody-Anti-Fugetactic Agent Complexes

In some embodiments, the antibody is conjugated to an effector moiety. The effector moiety can be any number of molecules, including labeling moieties such as radioactive labels or fluorescent labels, or can be a therapeutic moiety. In one aspect, the therapeutic moiety is a small molecule that modulates the activity of the tumor antigen. In another aspect, the therapeutic moiety modulates the activity of molecules associated with or in close proximity to the tumor antigen.

In other embodiments, the therapeutic moiety is a cytotoxic agent or anti-cancer agent. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin, auristatin and the like. Cytotoxic agents also include radiochemicals made by conjugating radioisotopes to antibodies raised against the tumor antigens, or binding of a radionuclide to a chelating agent that has been covalently attached to the antibody.

Binding Affinity of Antibodies

Binding affinity for a target tumor antigen is typically measured or determined by standard antibody-antigen assays, such as Biacore competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant (KD=1/K, where K is the affinity constant) of the antibody is <1 µM, preferably <100 nM, and most preferably <0.1 nM. Antibody molecules will typically have a KD in the lower ranges. KD=[Ab−Ag]/[Ab][Ag] where [Ab] is the concentration at equilibrium of the antibody, [Ag] is the concentration at equilibrium of the antigen and [Ab−Ag] is the concentration at equilibrium of the antibody-antigen complex. Typically, the binding interactions between antigen and antibody include reversible non-covalent associations such as electrostatic attraction, Van der Waals forces and hydrogen bonds.

In some embodiments, the antibodies bind to the tumor antigens with a KD of at least about 0.1 mM, more usually at least about 1 µM, preferably at least about 0.1 µM or less, and most preferably, 0.01 µM or less.

Anti-Fugetactic Agents

Many tumors have fugetactic effects, e.g. on immune cells, due to chemokines secreted by the tumor cells. High concentrations of the chemokines secreted by the tumor cells can have fugetactic (chemorepellant) effects on cells, whereas lower concentrations do not have such effects or even result in chemoattraction. For example, T-cells are repelled by CXCL12 (SDF-1) by a concentration-dependent and CXCR4-mediated mechanism. This invention is predicated, in part, on the surprising discovery that the antifugetactic agents as described herein reduce the fugetactic effects of the tumors, thereby allowing immune cells and other anti-cancer agents to better access and kill the tumor cells, and that complexation of an anti-fugetactic agent with an antibody to a tumor antigen can result in increased targeting of the agent to the tumor.

The anti-fugetactic agent may be any such agent known in the art, for example an anti-fugetactic agent as described in U.S. Patent Application Publication No. 2008/0300165, which is hereby incorporated by reference in its entirety.

Anti-fugetactic agents include any agents that specifically inhibit chemokine and/or chemokine receptor dimerization, thereby blocking the chemorepellent response to a fugetactic agent. Certain chemokines, including IL-8 and CXCL12 can also serve as chemorepellents at high concentrations (e.g., above 100 nM) where much of the chemokine exists as a dimer. Dimerization of the chemokine elicits a differential response in cells, causing dimerization of chemokine receptors, an activity which is interpreted as a chemorepellent signal. Blocking the chemorepellent effect of high concentrations of a chemokine secreted by a tumor can be accomplished, for example, by anti-fugetactic agents which inhibit chemokine dimer formation or chemokine receptor dimer formation. For example, antibodies that target and block chemokine receptor dimerization, for example, by interfering with the dimerization domains or ligand binding can be anti-fugetactic agents. Anti-fugetactic agents that act via other mechanisms of action, e.g. that reduce the amount of fugetactic cytokine secreted by the cells, inhibit dimerization, and/or inhibit binding of the chemokine to a target receptor, are also encompassed by the present invention. Where desired, this effect can be achieved without inhibiting the chemotactic action of monomeric chemokine.

In other embodiments, the anti-fugetactic agent is a CXCR4 antagonist, CXCR3 antagonist, CXCR4/CXCL12 antagonist or selective PKC inhibitor.

The CXCR4 antagonist can be but is not limited to AMD3100 (plerixafor), KRH-1636, T-20, T-22, T-140, TE-14011, T-14012, or TN14003, derivatives thereof, or an antibody that interferes with the dimerization of CXCR4. Additional CXCR4 antagonists are described, for example, in U.S. Patent Pub. No. 2014/0219952 and Debnath et al. *Theranostics*, 2013; 3(1): 47-75, each of which is incorporated herein by reference in its entirety, and include TG-0054 (burixafor), AMD3465, NIBR1816, AMD070, and derivatives thereof.

The CXCR3 antagonist can be but is not limited to TAK-779, AK602, or SCH-351125, or an antibody that interferes with the dimerization of CXCR3.

The CXCR4/CXCL12 antagonist can be but is not limited to Tannic acid, NSC 651016, or an antibody that interferes with the dimerization of CXCR4 and/or CXCL12.

The selective PKC inhibitor can be but is not limited to thalidomide or GF 109230X.

In a preferred embodiment, the anti-fugetactic agent is AMD3100 (plerixafor). AMD3100 is described in U.S. Pat. No. 5,583,131, which is incorporated by reference herein in its entirety.

In one embodiment, the anti-fugetactic agent is an AMD3100 derivative. AMD3100 derivatives include, but are not limited to, those found in U.S. Pat. Nos. 7,935,692 and 5,583,131 (USRE42152), each of which is incorporated herein by reference in its entirety.

In one embodiment, the anti-fugetactic agent is coupled with a molecule that allows targeting of a tumor. In one embodiment, the anti-fugetactic agent is coupled with (e.g., bound to or complexed with) an antibody specific for the tumor to be targeted. In one embodiment, the anti-fugetactic agent coupled to the molecule that allows targeting of the tumor is administered systemically.

In one embodiment, the anti-fugetactic agent is administered in combination with an additional compound that enhances the anti-fugetactic activity of the agent. In one embodiment, the additional compound is granulocyte colony stimulating factor (G-CSF). In one embodiment, G-CSF is not administered.

Antibody-Anti-Fugetactic Agent Complex

According to the method of this invention, an antibody-anti-fugetactic agent complex consists of a tumor-specific antibody linked to an anti-fugetactic agent. When introduced into the patient, the antibody component of the complex, which is reactive with an antigen found on the tumor cells, directs the complex to the site of the tumor and binds to the tumor cells. The antibody can therefore be viewed as delivering the anti-fugetactic agent to the site of the tumor. The complex can reach the tumor cells at that site, i.e., those cells bearing the particular tumor antigen to which the antibody of the complex is specific.

Furthermore, the present method does not require the anti-fugetactic agent to be bound directly to the antibody and thereby limit the amount of anti-fugetactic agent that can be delivered. Moreover, the present method is capable of releasing the anti-fugetactic agent specifically at the tumor site as opposed to release at other tissues. This is so because the concentration of the anti-fugetactic agent at the tumor site is higher than its concentration at other tissues due to the association of the tumor cells with the antibody-anti-fugetactic agent complex.

The antibody of the invention includes any antibody which binds specifically to a tumor-associated antigen. Examples of such antibodies include, but are not limited to, those which bind specifically to antigens found on carcinomas, melanomas, leukemia, lymphomas and bone and soft tissue sarcomas as well as other tumors.

These antibodies may be polyclonal or preferably, monoclonal, may be intact antibody molecules or fragments containing the active binding region of the antibody, e.g., Fab or F(ab')2, and can be produced using techniques well established in the art (see, e.g., R. A. DeWeger et al., "Eradication Of Murine Lymphoma And Melanoma Cells By Chlorambucil-Antibody Complexes, Immunological Rev., 62, pp. 29-45 (1982) (tumor-specific polyclonal antibodies produced and used in conjugates); M. Yeh et al., "Cell Surface Antigens Of Human Melanoma Identified By Monoclonal Antibody," Proc. Natl. Acad. Sci., 76, p. 2927 (1979); J. P. Brown et al. "Structural Characterization Of Human Melanoma-Associated Antigen p97 With Monoclonal Antibodies," J. Immunol., 127 (No. 2), pp. 539-546 (1981) (tumor-specific monoclonal antibodies produced); and J. P. Mach et al., "Improvement Of Colon Carcinoma Imaging: From Polyclonal Anti-CEA Antibodies And Static Photoscanning To Monoclonal Fab Fragments And ECT", in Monoclonal Antibodies For Cancer Detection And Therapy, R. W. Baldwin et al. (ed.s), pp. 53-64 (Academic Press 1985) (antibody fragments produced and used to localize to tumor cells)). In addition, if monoclonal antibodies are used, the antibodies may be of mouse or human origin or chimeric antibodies (see, e.g., V. T. Oi, "Chimeric Antibodies," Bio-Techniques 4 (No. 3). pp. 214-221 (1986)). In some embodiments, antibodies remain bound to the cell surface for extended periods or that are internalized very slowly.

The association of the antibody and anti-fugetactic agent in an antibody-anti-fugetactic agent complex may be through a covalent bond, a non-covalent bond, a carrier system, or other mechanism of interaction or association.

Non-Covalent Attachment

Alternative methods of attachment to antibody molecules outside the antigen-binding region (outside the variable domains) may involve use of antibodies directed against the constant domain of the antibody molecule, or use of Staphylococcal protein A which is known to bind specifically to a site on the constant region.

Non-covalent attachments include, for example and without limitation, ionic interactions, hydrogen bonding, Van der Waals forces, and hydrophobic interactions. Preferably, the non-covalent attachment is via hydrophobic interaction, e.g. between the anti-fugetactic agent and the antibody, optionally with another molecule (e.g., carrier molecule) that mediates the interaction.

Covalent Attachments

The present invention includes several methods for attaching compounds to antibody molecules: (1) attachment to the carbohydrate moieties of the antibody molecule, (2) attachment to sulfhydryl groups of the antibody molecule, and (3) attachment to amino or carboxy groups of the Fc region of the antibody molecule. Whichever method is used, the attachment must not significantly change the essential characteristics of the antibody, such as immunospecificity and immunoreactivity. Additional considerations include simplicity of reaction and stability of the antibody conjugate produced. In some embodiments, a linker molecule (e.g., linker polypeptide) is used to link the agent and the antibody.

The carbohydrate side chains of antibodies may be selectively oxidized to generate aldehydes. The resulting aldehydes may then be reacted with amine groups (e.g., ammonia derivatives such as hydroxylamine, hydrazine, phenylhydrazine, or semicarbazide) to form a Schiff base (e.g., oxime, hydrazone, phenylhydrazone or semicarbazone, respectively).

Alternatively, the carbohydrate moiety of the antibody may be modified by enzymatic techniques so as to enable attachment to or reaction with other chemical groups. One example of such an enzyme is galactose oxidase, which oxidizes galactose in the presence of oxygen.

Oxidation of the carbohydrate portion or moiety of antibody molecules leads to formation of aldehyde groups. A variety of oxidizing agents can be used, such as periodic acid, paraperiodic acid, sodium metaperiodate and potassum metaperiodate. Among these, oxygen acids and salts thereof are preferred since secondary or undesirable side reactions are less frequent. For a general discussion, see Jackson, 1944, Organic Reactions 2, p. 341; Bunton, 1965, Oxidation in Organic Chemistry, Vol. 1 (Wiberg, ed.), Academic Press, New York, p. 367.

Free sulfhydryl groups can be generated from the disulfide bonds of the immunoglobulin molecule. This is accomplished by mild reduction of the antibody molecule. The disulfide bonds of IgG, which are generally most susceptible to reduction, are those that link the two heavy chains. The disulfide bonds located near the antigen-binding region of the antibody molecule remain relatively unaffected. Such reduction results in the loss of ability to fix complement but does not interfere with antibody-antigen binding ability (Karush et al., 1979, Biochem. 18:2226-2232). The free sulfhydryl groups generated in the intra-heavy chain region can then react with iodoalkyl derivatives of any compound containing carboxy or amino groups (e.g., iodoalkyl derivatives of linker groups which are attached to a compound) to form a covalent linkage. Such linkage does not interfere with the antigen-binding site of the immunoglobulin.

Antibody conjugates which are produced by attaching a compound to free sulfhydryl groups of reduced immunoglobulin or reduced antibody fragments do not activate complement. Thus, these conjugates may be used for in vitro separation or in vivo imaging systems where cleavage and release of the compound is not desirable. Such conjugates may also be used when non-complement mediated release is desired. In such an embodiment, the compound may be linked to sulfhydryl groups on the reduced immunoglobulin, or reduced antibody fragments via linkers which are susceptible to cleavage by serum proteases.

Although attachment of a compound to sulfhydryl groups of the antibody molecule destroys complement fixation ability, such methods of attachment may be used to make antibody conjugates for use in the complement mediated release system. In such an embodiment, a compound joined to a complement sensitive substrate linker can be attached to sulfhydryls of reduced Ig molecules or antibody fragments and delivered to the target in a mixture with intact antibody molecules that are capable of activating complement. The latter would activate complement, which would cleave the compound from the former. The use of antibody fragments as carrier molecules in the complement mediated release system would permit the treatment of pregnant females, and offers the advantage of more rapid penetration of the conjugate into target sites.

Conventional methods for linking compounds to antibody molecules may also be used for the purposes of the present invention. These conventional methods attach compounds to amino or carboxy groups of the antibody molecule. A disadvantage of conventional methods is a decreased binding affinity of the antibody molecule for antigen (i.e., a decreased immunospecific activity) because of non-specific binding of the linkers or compounds to the Fab region (antigen binding arms) of the antibody molecule. Thus, in order to utilize conventional linking methods, the substrate linker should be directed to a more optimal position on the antibody molecule to allow immune complex formation and cleavage by complement. To this end, the antigen-binding arms (Fab regions) of the immunoglobulin or half-molecules are protected while either the amino or carboxy groups of the Fc region are reacted with a substrate linker.

Carrier Systems

A number of agents have been utilized as carrier molecules with limited success in drug delivery systems. In practice the carrier should be non-toxic and target site specific. Ideally there should be a mechanism for release of the active form of the compound from the carrier at the target site. Carrier molecules such as albumin (e.g., human serum albumin [HSA], including recombinant HSA), DNA, liposomes, proteins, steroid hormones, and the like have been used in conjunction with a broad spectrum of pharmaceutical or cytotoxic agents such as: radioactive compounds; agents which bind DNA, for instance, alkylating agents or various antibiotics (e.g., daunomycin, adriamycin, chlorambucil); antimetabolites such as methotrexate; agents which act on cell surfaces (e.g., venom phospholipases and microbial toxins); and protein synthesis inhibitors (e.g., diphtheria toxin and toxic plant proteins). For reviews on the subject see Bale et al., 1980, Cancer Research 40:2965-2972; Ghose and Blair, 1978, J. Natl. Cancer Inst. 61(3):657-676: Gregoriadis, 1977, Nature 265:407-411; Gregoriadis, 1980, Pharmac. Ther. 10:103-118; Trouet et al., 1980, Recent Results Cancer Res. 75:229-235.

Liposome mediated delivery of pharmaceutical agents has major drawbacks because of its lack of target specificity. Recently, investigators have attempted to overcome this problem by covalently attaching whole antibody or Fab fragments to liposomes containing a pharmaceutical agent (Heath et al., 1981, Biochim. Biophys. Acta 640:66-81; Huang et al., 1980, J. Biol. Chem. 255(17):8015-8018; Jansons and Mallet, 1981. Anal. Biochem. 111:54-59, Martin et al., 1981, Biochem. 20:4229-4238). Others have reported the coupling of protein A (Staph A protein) to liposomes in order to direct the preparation to multiple specific targets which have previously been bound to antibodies. Such targets are simply limited by the antibodies used (Leserman et al., 1980, Nature 288:602-604).

In other embodiments, the antibody-anti-fugetactic agent complex comprises a carrier system. For example, the antibody is bound to a liposome or particle containing the anti-fugetactic agent. In some embodiments, the carrier system comprises an albumin complex, optionally including a chemotherapeutic agent (e.g., paclitaxel). Non-limiting examples of albumin-antibody complexes and methods of making can be found in PCT Pub. Nos. 2012/154861, 2014/055415, and 2016/057554, each of which is incorporated herein by reference in its entirety.

Anti-Cancer (Cancer Therapeutic) Agents

Table 2 depicts a list of non-limiting list of cancer therapeutic agents.

TABLE 2

Anti-cancer (cancer therapeutic) agents
Cancer Drugs

| Drug | Target(s) |
| --- | --- |
| Abitrexate (Methotrexate) | Acute lymphoblastic leukemia; breast cancer; gestational trophoblastic disease, head and neck cancer; lung cancer; mycosis fungoides; non-Hodgkin lymphoma; osteosarcoma |
| Abraxane (Paclitaxel Albumin-stabilized Nanoparticle Formulation) | Breast cancer; non-small cell lung cancer; pancreatic cancer |
| ABVD (Adriamycin, bleomycin, vinblastine sulfate, dacarbazine) | Hodgkin lymphoma |
| ABVE (Adriamycin, bleomycin, vincristine sulfate, etoposide) | Hodgkin lymphoma (in children) |
| ABVE-PC(Adriamycin, bleomycin, vincristine sulfate; etoposide, prednisone, cyclophosphamide) | Hodgkin lymphoma (in children) |
| AC (Adriamycin cyclophosphamide) | Breast cancer |
| AC-T (Adriamycin, cylclophosphamide, Taxol) | Breast cancer |
| Adcetris (Brentuximab Vedotin) | Anaplastic large cell lymphoma; Hodgkin lymphoma |
| ADE (Cytarabine (Ara-C), Daunorubicin Hydrochloride, Etoposide) | Acute myeloid leukemia (in children) |
| Ado-Trastuzumab Emtansine | Breast cancer |
| Adriamycin (Doxorubicin Hydrochloride) | Acute lymphoblastic leukemia; acute myeloid leukemia; breast cancer; gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor |
| Adrucil (Fluorouracil) | Basal cell carcinoma; breast cancer; colorectal cancer; gastric (stomach) adenocarcinoma; pancreatic cancer; squamous cell carcinoma of the head and neck |

TABLE 2-continued

Anti-cancer (cancer therapeutic) agents
Cancer Drugs

| Drug | Target(s) |
| --- | --- |
| Afatinib Dimaleate | Non-small cell lung cancer |
| Afinitor (Everolimus) | Breast cancer, pancreatic cancer; renal cell carcinoma; subependymal giant cell astrocytoma |
| Alimta (Pemetrexed Disodium) | Malignant pleural mesothelioma; non-small cell lung cancer |
| Ambochlorin (Chlorambucil) | Chronic lymphocytic leukemia; Hodgkin lymphoma; non-Hodgkin lymphoma |
| Anastrozole | Breast cancer |
| Aredia (Pamidronate Disodium) | Breast cancer; multiple myeloma |
| Arimidex (Anastrozole) | Breast cancer |
| Aromasin (Exemestane) | Advanced breast cancer; early-stage breast cancer and estrogen receptor positive |
| Arranon (Nelarabine) | T-cell acute lymphoblastic leukemia; T-cell lymphoblastic lymphoma |
| Azacitidine | Myelodysplastic syndromes |
| BEACOPP | Hodgkin lymphoma |
| Becenum (Carmustine) | Brain tumors; Hodgkin lymphoma; multiple myeloma; non-Hodgkin lymphoma |
| Beleodaq (Belinostat) | Peripheral T-cell lymphoma |
| BEP | Ovarian germ cell tumors; testicular germ cell tumors |
| Bicalutamide | Prostate cancer |
| BiCNU (Carmustine) | Brain tumors; Hodgkin lymphoma; multiple myeloma; non-Hodgkin lymphoma |
| Bleomycin | Hodgkin lymphoma; non-Hodgkin lymphoma; penile cancer; squamous cell carcinoma of the cervix; squamous cell carcinoma of the head and neck; squamous cell carcinoma of the vulva; testicular cancer |
| Bosulif (Bosutinib) | Chronic myelogenous leukemia |
| Brentuximab Vedotin | Anaplastic large cell lymphoma; Hodgkin lymphoma |
| Busulfan | Chronic myelogenous leukemia |
| Busulfex (Busulfan) | Chronic myelogenous leukemia |
| Cabozantinib-S-Malate | Medullary thyroid cancer |
| CAF | Breast cancer |
| Camptosar (Irinotecan Hydrochloride) | Colorectal cancer |
| CAPOX | Colorectal cancer |
| Carfilzomib | Multiple myeloma |
| Casodex (Bicalutamide) | Prostate cancer |
| CeeNU (Lomustine) | Brain tumors; Hodgkin lymphoma |
| Ceritinib | Non-small cell lung cancer |
| Cerubidine (Daunorubicin Hydrochloride) | Acute lymphoblastic leukemia; acute myeloid leukemia |
| Chlorambucil | Chronic lymphocytic leukemia; Hodgkin lymphoma; non-Hodgkin lymphoma |
| CHLORAMBUCIL-PREDNISONE | Chronic lymphocytic leukemia |
| CHOP | Non-Hodgkin lymphoma |
| Cisplatin | Bladder cancer; cervical cancer; malignant mesothelioma; non-small cell lung cancer; ovarian cancer; squamous cell carcinoma of the head and neck; testicular cancer |
| Clafen (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma |
| Clofarex (Clofarabine) | Acute lymphoblastic leukemia |
| CMF | Breast cancer |
| Cometriq (Cabozantinib-S-Malate) | Medullary thyroid cancer |
| COPP | Hodgkin lymphoma; non-Hodgkin lymphoma |
| COPP-ABV | Hodgkin lymphoma |
| Cosmegen (Dactinomycin) | Ewing sarcoma; gestational trophoblastic disease; rhabdomyosarcoma; solid tumors; testicular cancer; Wilms tumor |

TABLE 2-continued

Anti-cancer (cancer therapeutic) agents
Cancer Drugs

| Drug | Target(s) |
|---|---|
| CVP | Non-Hodgkin lymphoma; chronic lymphocytic leukemia |
| Cyclophosphamide | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma. |
| Cyfos (Ifosfamide) | Testicular germ cell tumors |
| Cyramza (Ramucirumab) | Adenocarcinoma; colorectal cancer; non-small cell lung cancer |
| Cytarabine | Acute lymphoblastic leukemia; acute myeloid leukemia; chronic myelogenous leukemia; meningeal leukemia |
| Cytosar-U (Cytarabine) | Acute lymphoblastic leukemia; acute myeloid leukemia; chronic myelogenous leukemia; meningeal leukemia |
| Cytoxan (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma.; non-Hodgkin lymphoma; ovarian cancer; retinoblastoma |
| Dacarbazine | Hodgkin lymphoma; melanoma |
| Dacogen (Decitabine) | Myelodysplastic syndromes |
| Dactinomycin | Ewing sarcoma; gestational trophoblastic disease; rhabdomyosarcoma; solid tumors; testicular cancer; Wilms tumor |
| Daunorubicin Hydrochloride | Acute lymphoblastic leukemia; acute myeloid leukemia |
| Degarelix | Prostate cancer |
| Denileukin Diftitox | Cutaneous T-cell lymphoma |
| Denosumab | Giant cell tumor of the bone; breast cancer, prostate cancer |
| DepoCyt (Liposomal Cytarabine) | Lymphomatous meningitis |
| DepoFoam (Liposomal Cytarabine) | Lymphomatous meningitis |
| Docetaxel | Breast cancer; adenocarcinoma of the stomach or gastroesophageal junction; non-small cell lung cancer; prostate cancer; squamous cell carcinoma of the head and neck |
| Doxil (Doxorubicin Hydrochloride Liposome) | AIDS-related Kaposi sarcoma; multiple myeloma; ovarian cancer |
| Doxorubicin Hydrochloride | Acute lymphoblastic leukemia; acute myeloid leukemia; breast cancer; gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor. |
| Dox-SL (Doxorubicin Hydrochloride Liposome) | AIDS-related Kaposi sarcoma; multiple myeloma; ovarian cancer |
| DTIC-Dome (Dacarbazine) | Hodgkin lymphoma; melanoma |
| Efudex (Fluorouracil) | Basal cell carcinoma; breast cancer; colorectal cancer; gastric (stomach) adenocarcinoma; pancreatic cancer; squamous cell carcinoma of the head and neck |
| Ellence (Epirubicin Hydrochloride) | Breast cancer |
| Eloxatin (Oxaliplatin) | Colorectal cancer; stage III colon cancer |
| Emend (Aprepitant) | Nausea and vomiting caused by chemotherapy and nausea and vomiting after surgery |
| Enzalutamide | Prostate cancer |
| Epirubicin Hydrochloride | Breast cancer |

TABLE 2-continued

Anti-cancer (cancer therapeutic) agents
Cancer Drugs

| Drug | Target(s) |
|---|---|
| EPOCH | Non-Hodgkin lymphoma |
| Erbitux (Cetuximab) | Colorectal cancer; squamous cell carcinoma of the head and neck |
| Eribulin Mesylate | Breast cancer |
| Erivedge (Vismodegib) | Basal cell carcinoma |
| Erlotinib Hydrochloride | Non-small cell lung cancer; pancreatic cancer |
| Erwinaze (Asparaginase Erwinia chrysanthemi) | Acute lytnphoblastic leukemia |
| Etopophos (Etoposide Phosphate) | Small cell lung cancer; testicular cancer |
| Evacet (Doxorubicin Hydrochloride Liposome) | AIDS-related Kaposi sarcoma; multiple myeloma; ovarian cancer |
| Everolimus | Breast cancer; pancreatic cancer; renal cell carcinoma; subependymal giant cell astrocytoma |
| Evista (Raloxifene Hydrochloride) | Breast cancer |
| Exemestane | Breast cancer |
| Fareston (Toremifene) | Breast cancer |
| Farydak (Panobinostat) | Multiple myeloma |
| Faslodex (Fulvestrant) | Breast cancer |
| FEC | Breast cancer |
| Femara (Letrozole) | Breast cancer |
| Filgrastim | Neutropenia |
| Fludara (Fludarabine Phosphate) | Chronic lymphocytic leukemia |
| Fluoroplex (Fluorouracil) | Basal cell carcinoma; breast cancer; colorectal cancer; gastric (stomach) adenocarcinoma; pancreatic cancer; squamous cell carcinoma of the head and neck |
| Folex (Methotrexate) | Acute lymphoblastic leukemia; breast cancer; gestational trophoblastic disease; head and neck cancer; lung cancer; mycosis fungoides; non-Hodgkin lymphoma; osteosarcoma |
| FOLFIRI | Colorectal cancer |
| FOLFIRI-BEVACIZUMAB | Colorectal cancer |
| FOLFIRI-CETUXIMAB | Colorectal cancer |
| FOLFIRINOX | Pancreatic cancer |
| FOLFOX | Colorectal cancer |
| Folotyn (Pralatrexate) | Peripheral T-cell lymphoma |
| FU-LV | Colorectal cancer; esophageal cancer; gastric cancer |
| Fulvestrant | Breast cancer |
| Gefitinib | Non-small cell lung cancer |
| Gemcitabine Hydrochloride | Breast cancer; non-small cell lung cancer; ovarian cancer; pancreatic cancer |
| GEMCITABINE-CISPLATIN | Biliary tract cancer; bladder cancer; cervical cancer; malignant mesothelioma; non-small cell lung cancer; ovarian cancer; pancreatic cancer |
| GEMCITABINE-OXALIPLATIN | Pancreatic cancer |
| Gemtuzumab Ozogamicin (antibody drug conjugate) | Acute myeloid leukemia |
| Gemzar (Gemcitabine Hydrochloride) | Breast cancer; non-small cell lung cancer; ovarian cancer; pancreatic cancer |
| Gilotrif(Afatinib Dimaleate) | Non-small cell lung cancer |
| Gleevec (Imatinib Mesylate) | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |
| Gliadel (Carmustine Implant) | Glioblastoma multiforme; malignant glioma |

TABLE 2-continued

Anti-cancer (cancer therapeutic) agents
Cancer Drugs

| Drug | Target(s) |
|---|---|
| Goserelin Acetate | Breast cancer; prostate cancer |
| Halaven (Eribulin Mesylate) | Breast cancer |
| Hycamtin (Topotecan Hydrochloride) | Cervical cancer; ovarian cancer; small cell lung cancer |
| Hyper-CVAD | Acute lymphoblastic leukemia; non-Hodgkin lymphoma |
| Ibrance (Palbociclib) | Breast cancer |
| Ibrutinib | Chronic lymphocytic leukemia; mantel cell lymphoma; |
| ICE | Hodgkin lymphoma; non-Hodgkin lymphoma |
| Iclusig Ponatinib Hydrochloride | Acute lymphoblastic leukemia; Chronic myelogenous leukemia |
| Idamycin (Idarubicin Hydrochloride) | Acute myeloid leukemia |
| Imatinib Mesylate | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |
| Imbruvica (Ibrutinib) | Chronic lymphocytic leukemia; mantle cell lymphoma; Waldenström macroglobulinemia |
| Inlyta (Axitinib) | Renal cell carcinoma |
| Iressa (Gefitinib) | Non-small cell lung cancer |
| Irinotecan Hydrochloride | Colorectal cancer |
| Istodax (Romidepsin) | Cutaneous T-cell lymphoma |
| Ixempra (Ixabepilone) | Breast cancer |
| Jevtana (Cabazitaxel) | Prostate cancer |
| Keoxifene (Raloxifene Hydrochloride) | Breast cancer |
| Kyprolis (Carfilzomib) | Multiple myeloma |
| Lenvima (Lenvatinib Mesylate) | Thyroid cancer |
| Letrozole | Breast cancer |
| Leucovorin Calcium | Colorectal cancer |
| Leukeran (Chlorambucil) | Chronic lymphocytic leukemia; Hodgkin lymphoma; non-Hodgkin lymphoma |
| Leuprolide Acetate | Prostate cancer |
| Linfolizin (Chlorambucil) | Chronic lymphocytic leukemia; Hodgkin lymphoma; non-Hodgkin lymphoma |
| LipoDox (Doxorubicin Hydrochloride Liposome) | AIDS-related Kaposi sarcoma; multiple myeloma; ovarian cancer |
| Lomustine | Brain tumors; Hodgkin lymphoma |
| Lupron (Leuprolide Acetate) | Prostate cancer |
| Lynparza (Olaparib) | Ovarian cancer |
| Marqibo (Vincristine Sulfate Liposome) | Acute lymphoblastic leukemia |
| Matulane (Procarbazine Hydrochloride) | Hodgkin lymphoma |
| Mechlorethamine Hydrochloride | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Megace (Megestrol Acetate) | Breast cancer; endometrial cancer |
| Mekinist (Trametinib) | Melanoma |
| Mercaptopurine | Acute lymphoblastic leukemia |
| Mesnex (Mesna) | Hemorrhagic cystitis |
| Methazolastone (Temozolomide) | Anaplastic astrocytoma; glioblastoma multiforme |
| Mexate (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mexate-AQ (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mitoxantrone Hydrochloride | Acute myeloid leukemia; prostate cancer |
| Mitozytrex (Mitomycin C) | Gastric (stomach) and pancreatic adenocarcinoma |
| MOPP | Hodgkin lymphoma |
| Mozobil (Plerixafor) | Multiple myeloma; non-Hodgkin lymphoma |
| Mustargen (Mechlorethamine Hydrochloride) | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Myleran (Busulfan) | Chronic myelogenous leukemia |
| Mylotarg (Gemtuzumab Ozogamicin) | Acute myeloid leukemia |
| Nanoparticle Paclitaxel (Paclitaxel Albumin-stabilized Nanoparticle Formulation) | Breast cancer; Non-small cell lung cancer; Pancreatic cancer |
| Navelbine (Vinorelbine Tartrate) | Non-small cell lung cancer |
| Nelarabine | T-cell acute lymphoblastic leukemia |
| Neosar (Cyclophosphamide) | Acute lymphoblastic leukemia; Acute myeloid leukemia; Breast cancer; Chronic lymphocytic leukemia; Chronic myelogenous leukemia; Hodgkin lymphoma; Multiple myeloma; Mycosis fungoides; Neuroblastoma; Non-Hodgkin lymphoma; Ovarian cancer; Retinoblastoma |
| Nexavar (Sorafenib Tosylate) | Hepatocellular carcinoma; Renal cell carcinoma; Thyroid cancer |
| Nilotinib | Chronic myelogenous leukemia |
| Nivolumab | Melanoma; Squamous non-small cell lung cancer |
| Nolvadex (Tamoxifen Citrate) | Breast cancer |
| Odomzo Sonidegib) | Basal cell carcinoma |
| OEPA | Hodgkin lymphoma |
| OFF | Pancreatic cancer |
| Olaparib | Ovarian cancer |
| Oncaspar (Pegaspargase) | Acute lymphoblastic leukemia |
| OPPA | Hodgkin lymphoma |
| Oxaliplatin | Colorectal cancer; Stage III colon cancer |
| Paclitaxel | AIDS-related Kaposi sarcoma; Breast cancer; Non-small cell tuna cancer; Ovarian cancer |
| Paclitaxel Albumin-stabilized Nanoparticle Formulation | Breast cancer; Non-small lung cancer; Pancreatic cancer |
| PAD | Multiple myeloma |
| Palbociclib | Breast cancer |
| Pamidronate Disodium | Breast cancer; Multiple myeloma |
| Panitumumab | Colorectal cancer |
| Panobinostat | Multiple myeloma |
| Paraplat (Carboplatin) | Non-small cell lung cancer; Ovarian cancer |
| Paraplatin (Carboplatin) | Non-small cell lung cancer; Ovarian cancer |
| Pazopanib Hydrochloride | Renal cell carcinoma; Soft tissue sarcoma |
| Pegaspargase | Acute lymphoblastic leukemia |
| Pemetrexed Disodium | Malignant pleural mesothelioma; Non-small cell lung cancer |
| Platinol (Cisplatin) | Bladder cancer; Cervical cancer; Malignant mesothelioma; Non-small cell lung cancer; Ovarian cancer; Squamous cell carcinoma of the head and neck; Testicular cancer |

TABLE 2-continued

Anti-cancer (cancer therapeutic) agents
Cancer Drugs

| Drug | Target(s) |
|---|---|
| Platinal-AQ (Cisplatin) | Bladder cancer; Cervical cancer; Malignant mesothelioma; Non-small cell lung cancer; Ovarian cancer; Squamous cell carcinoma of the head and neck; Testicular cancer |
| Plerixafor | Multiple myeloma; Non-Hodgkin lymphoma |
| Pomalidomide | Multiple myeloma |
| Pomalyst (Pomalidomide) | Multiple myeloma |
| Pontinib Hydrochloride | Acute lymphoblastic leukemia; Chronic myelogenous leukemia |
| Pralatrexate | Peripheral T-cell lymphoma |
| Prednisone | Acute lymphoblastic leukemia; Chronic lymphocytic leukemia; Hodgkin lymphoma; Multiple myeloma; Non-Hodgkin lymphoma; Prostate cancer; Thymoma and thymic carcinoma |
| Procarbazine Hydrochloride | Hodgkin lymphoma |
| Provenge (Sipuleucel-T) | Prostate cancer |
| Purinethol (Mercaptopurine) | Acute lymphoblastic leukemia |
| Radium 223 Dichloride | Prostate cancer |
| Raloxifene Hydrochloride | Breast cancer |
| R-CHOP | Non-Hodgkin lymphoma |
| R-CVP | Non-Hodgkin lymphoma |
| Regorafenib | Colorectal cancer; Gastrointestinal stromal tumor |
| R-EPOCH | B-cell non-Hodgkin lymphoma |
| Revlimid (Lenalidomide) | Mantle cell lymphoma; Multiple myeloma; Anemia |
| Rheumatrex (Methotrexate) | Acute lymphoblastic leukemia; Breast cancer; Gestational trophoblastic disease; Head and neck cancer; Lung cancer; Non-Hodgkin lymphoma; Osteosarcoma |
| Romidepsin | Cutaneous T-cell lymphoma |
| Rubidomycin (Daunorubicin Hydrochloride) | Acute lymphoblastic leukemia; Acute myeloid leukemia |
| Sipuleucel-T | Prostate cancer |
| Somatuline Depot (Lanreotide Acetate) | Gastroenteropancreatic neuroendocrine tumors |
| Sonidegib | Basal cell carcinoma |
| Sorafenib Tosylate | Hepatocellular carcinoma; Renal cell carcinoma; Thyroid cancer |
| Sprycel (Dasatinib) | Acute lymphoblastic leukemia; Chronic myelogenous leukemia |
| STANFORD V | Hodgkin lymphoma |
| Stivarga (Regorafenib) | Colorectal cancer; Gastrointestinal stromal tumor |
| Sunitinb Malate | Gastronintestinal stromal tumor; Pancreatic cancer; Renal cell carcinoma |
| Sutent (Sunitinib Malate) | Gastronintestinal stromal tumor; Pancreatic cancer; Renal cell carcinoma |
| Synovir (Thalidomide) | Multiple myeloma |
| Synribo (Omacetaxine Mepesuccinate) | Chronic myelogenous leukemia |
| TAC | Breast cancer |
| Tafinlar (Dabrafenib) | Melanoma |
| Tamoxifen Citrate | Breast cancer |
| Tarabine PFS (Cytarabine) | Acute lymphoblastic leukemia; Acute myeloid leukemia; Chronic myelogenous leukemia |
| Tarceva (Erlotinib Hydrochloride) | Non-small cell lung cancer; Pancreatic cancer |
| Targretin (Bexarotene) | Skin problems caused by cutaneous T-cell lymphoma |
| Tasigna (Niltinib) | Chronic myelogenous leukemia |
| Taxol (Paclitaxel) | AIDS-related Kaposi sarcoma; Breast cancer; Non-small cell lung cancer; Ovarian cancer |
| Taxotere (Docetaxel) | Breast cancer; Adenocarcinoma; Non-small cell lung cancer; Prostate cancer; Squamous cell carcinoma of the head and neck |
| Temodar (Temozolomide) | Anaplastic astrocytoma; Glioblastoma multiforme |
| Temozolomide | Anaplastic astrocytoma; Glioblastoma multiforme |
| Thiotepa | Bladder cancer; Breast cancer; Malignant pleural effusion, malignant pericardial effusion, and malignant peritoneal effusion; Ovarian cancer |
| Toposar (Etoposide) | Small cell lung cancer; Testicular cancer |
| Topotecan Hydrochloride | Cervical cancer; Ovarian cancer; Small cell lung cancer |
| Toremifene | Breast cancer |
| Torisel (Temsirolimus) | Renal cell carcinoma |
| TPF | Squamous cell carcinoma of the head and neck; Gastric (stomach) cancer |
| Trastuzumab | Adenocarcinoma; Breast cancer |
| Treanda (Bendamustine Hydrochloride) | B-cell non-Hodgkin lymphoma; Chronic lymphocytic leukemia |
| Trisenox (Arsenic Trioxide) | Acute promyelocytic leukemia |
| Tykerb (Lapatinib Ditosylate) | Breast cancer |
| Vandetabib | Medullary thyroid cancer |
| VAMP | Hodgkin lymphoma |
| VeIP | Ovarian germ cell; Testicular cancer |
| Velban (Vinblastine Sulfate) | Breast cancer; Choriocarcinoma; Hodgkin lymphoma; Kaposi sarcoma; Mycosid fungoides; Non-Hodgkin lymphoma; Testicular cancer |
| Velcade (Bortezomib) | Mulitple myeloma; Mantle cell lymphoma |
| Velsar (Vinblastine Sulfate) | Breast cancer; Choriocarcinoma; Hodgkin lymphoma; Kaposi sarcoma; Mycosis fungoides; Non-Hodgkin lymphoma; Testicular cancer |
| VePesid (Etoposide) | Small cell lung cancer; Testicular cancer |
| Viadur (Leuprolide Acetate) | Prostate cancer |
| Vidaza (Azacitidine) | Myelodysplastic syndromes |
| Vincasar PFS (Vincristine Sulfate) | Acute leukemia; Hodgkin lymphoma; Neuroblastoma; Non-Hodgkin lymphoma; Rhabdomyosarcoma; Wilms tumor |
| Vincristine Sulfate Liposome | Acute lymphoblastic leukemia |
| Vinorelbine Tartrate | Non-small cell lung cancer |
| VIP | Testicular cancer |
| Visbodegib | Basal cell carcinoma |
| Voraxaze (Glucarpidase) | Toxic blood levels of the anticancer drug methotrexate |
| Votrient (Pazopanib Hydrochloride) | Renal cell carcinoma; Soft tissue sarcoma. |
| Wellcovorin (Leucovorin Calcium) | Colorectal cancer; Anemia |
| Xalkori (Crizotinib) | Non-small cell lung cancer |
| Xeloda (Capecitabine) | Breast cancer; Colorectal cancer |
| XELIRI | Colorectal cancer; Esophageal cancer; Gastric (stomach) cancer |
| XELOX | Colorectal cancer |
| Xofigo (Radium 223 Dichloride) | Prostate cancer |
| Xtandi Enzalutamide) | Prostate cancer |
| Zaltrap (Ziv-Aflibercept) | Colorectal cancer |
| Zelboraf (Vemurafenib) | Melanoma |
| Ziv-Aflibercept | Colorectal cancer |
| Zoladex (Goserelin Acetate) | Breast cancer; Prostate cancer |
| Zolinza (Vorinostat) | Cutaneous T-cell lymphoma |
| Zometa (Zoledronic Acid) | Multiple myeloma |

TABLE 2-continued

Anti-cancer (cancer therapeutic) agents
Cancer Drugs

| Drug | Target(s) |
| --- | --- |
| Zydelig (Idelalisib) | Chronic lymphocytic leukemia; Non-Hodgkin lymphoma (Follicula B-cell non Hodgkin lymphoma and Small lymphocytic lymphoma) |
| Zykadia (Certinib) | Non-small cell lung cancer |
| Zytiga (Abiraterone Acetate) | Prostate cancer |

Immunotherapy Agents
Natural Killer Cells

In some embodiments, the immunotherapy agent comprises natural killer cells. Natural killer (NK) cells are a class of lymphocytes that typically comprise approximately 10% of the lymphocytes in a human. NK cells provide an innate cellular immune response against tumor and infected (target) cells. NK cells, which are characterized as having a CD3-/CD56+ phenotype, display a variety of activating and inhibitory cell surface receptors. NK cell inhibitory receptors predominantly engage with major histocompatibility complex class I ("MHC-I") proteins on the surface of a normal cell to prevent NK cell activation. The MHC-I molecules define cells as "belonging" to a particular individual. It is thought that NK cells can be activated only by cells on which these "self" MHC-I molecules are missing or defective, such as is often the case for tumor or virus-infected cells.

NK cells are triggered to exert a cytotoxic effect directly against a target cell upon binding or ligation of an activating NK cell receptor to the corresponding ligand on the target cell. The cytotoxic effect is mediated by secretion of a variety of cytokines by the NK cells, which in turn stimulate and recruit other immune system agents to act against the target. Activated NK cells also lyse target cells via the secretion of the enzymes perforin and granzyme, stimulation of apoptosis-initiating receptors, and other mechanisms.

NK cells have been evaluated as an immunotherapeutic agent in the treatment of certain cancers. NK cells used for this purpose may be autologous or non-autologous (i.e., from a donor).

In one embodiment, the NK cells used in the compositions and methods herein are autologous NK cells. In one embodiment, the NK cells used in the compositions and methods herein are non-autologous NK cells.

In one embodiment, the NK cells used in the compositions and methods herein are modified NK cells. NK cells can be modified by insertion of genes or RNA into the cells such that the cells express one or more proteins that are not expressed by wild type NK cells. In one embodiment, the NK cells are modified to express a chimeric antigen receptor (CAR). In a preferred embodiment, the CAR is specific for the cancer being targeted by the method or composition.

Non-limiting examples of modified NK cells can be found, for example, in Glienke, et al. 2015, Advantages and applications of CAR-expressing natural killer cells, *Frontiers in Pharmacol.* 6, article 21; PCT Patent Pub. Nos. WO 2013154760 and WO 2014055668; each of which is incorporated herein by reference in its entirety.

NK-92 Cells

In some embodiments, the NK cells are NK-92 cells. The NK-92 cell line was discovered in the blood of a subject suffering from a non-Hodgkins lymphoma. NK-92 cells lack the major inhibitory receptors that are displayed by normal NK cells, but retain a majority of the activating receptors. NK-92 cells are cytotoxic to a significantly broader spectrum of tumor and infected cell types than are NK cells and often exhibit higher levels of cytotoxicity toward these targets. NK-92 cells do not, however, attack normal cells, nor do they elicit an immune rejection response. In addition, NK-92 cells can be readily and stably grown and maintained in continuous cell culture and, thus, can be prepared in large quantities under c-GMP compliant quality control. This combination of characteristics has resulted in NK-92 being entered into presently on-going clinical trials for the treatment of multiple types of cancers.

NK-92 cells used in the compositions and methods described herein may be wild type (i.e., not genetically modified) NK-92 cells or genetically modified NK-92 cells. NK-92 cells can be genetically modified by insertion of genes or RNA into the cells such that the cells express one or more proteins that are not expressed by wild type NK-92 cells. In one embodiment, NK-92 cells are genetically modified to express a chimeric antigen receptor (CAR) on the cell surface. In a preferred embodiment, the CAR is specific for the cancer being targeted by the method or composition. In one embodiment, NK-92 cells are genetically modified to express an Fc receptor on the cell surface. In a preferred embodiment, the NK-92 cell expressing the Fc receptor can mediate antibody-dependent cell-mediated cytotoxicity (ADCC). In one embodiment, the Fc receptor is CD16. In one embodiment, NK-92 cells are genetically modified to express a cytokine (e.g., IL-2).

In one embodiment, the modified NK-92 cell is administered in combination with an antibody specific for the cancer to be treated. In a preferred embodiment, the modified NK-92 cell administered in combination with the antibody is competent to mediate ADCC. Examples of NK-92 cells are available from the American Type Culture Collection (ATCC) as ATCC CRL-2407.

Non-limiting examples of modified NK-92 cells are described, for example, in U.S. Pat. Nos. 7,618,817 and 8,034,332; and U.S. Patent Pub. Nos. 2002/0068044 and 2008/0247990, each of which is incorporated herein by reference in its entirety. Examples of modified NK-92 cells are available from ATCC as ATCC CRL-2408, ATCC CRL-2409, PTA-6670, PTA-6967, PTA-8837, and PTA-8836. Non-limiting examples of CAR-modified NK-92 cells can be found, for example, in Glienke, et al. 2015, Advantages and applications of CAR-expressing natural killer cells, *Frontiers in Pharmacol.* 6, article 21; which is incorporated herein by reference in its entirety.

T Cells

In one embodiment, the immunotherapy agent comprises T cells. T cells are lymphocytes having T-cell receptor in the cell surface. T cells play a central role in cell-mediated immunity by tailoring the body's immune response to specific pathogens. T cells, especially modified T cells, have shown promise in reducing or eliminating tumors in clinical trials. Generally, such T cells are modified and/or undergo adoptive cell transfer (ACT). ACT and variants thereof are well known in the art. See, for example, U.S. Pat. Nos. 8,383,099 and 8,034,334, which are incorporated herein by reference in their entireties.

U.S. Patent App. Pub. Nos. 2014/0065096 and 2012/0321666, incorporated herein by reference in their entireties, describe methods and compositions for T cell or NK cell treatment of cancer. T cells can be activated and expanded generally using methods as described, for example, in U.S. Pat. Nos. 6,352,694; 6,534,055; 6,905,680; 6,692,964;

5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 2006/0121005, each of which is incorporated herein by reference in its entirety.

In one embodiment, the T cells used in the compositions and methods herein are autologous T cells (i.e., derived from the patient). In one embodiment, the T cells used in the compositions and methods herein are non-autologous (heterologous or allogenic; e.g. from a donor or cell line) T cells. In one embodiment, the T cell is a cell line derived from T cell(s) or cancerous/transformed T cell(s).

In a preferred embodiment, the T cell used in the methods and compositions described herein is a modified T cell. In one embodiment, the T cell is modified to express a CAR on the surface of the T cell. In a preferred embodiment, the CAR is specific for the cancer being targeted by the method or composition. In one embodiment, the T cell is modified to express a cell surface protein or cytokine. Non-limiting examples of modified T cells are described in U.S. Pat. No. 8,906,682; PCT Patent Pub. Nos. WO 2013154760 and WO 2014055668; each of which is incorporated herein by reference in its entirety.

In one embodiment, the T cell is a T cell line. T cell lines include T-ALL cell lines, as described in U.S. Pat. No. 5,272,082, which is incorporated herein by reference in its entirety.

In another alternative embodiment, the immunotherapeutic agent is a T cell. In some embodiments, the T cell is a CAR T cell.

In one embodiment, T cells specific for particular tumor antigens can be transformed and expanded ex vivo and re-infused into patients. Without being bound by a particular theory or mode of action, an ex vivo autologous T cell population, obtained from a mammalian patient having a cancerous tumor having varying concentrations of an anti-fugetactic agent (e.g., AMD3100) bound to individual T cells through its CXCR4 receptors, exhibits overall anti-fugetactic properties in vivo relative to the tumor in the patient.

Antibodies

Immunotherapy also refers to treatment with anti-tumor antibodies. That is, antibodies specific for a particular type of cancer (e.g., a cell surface protein expressed by the target cancer cells) can be administered to a patient having cancer. The antibodies may be monoclonal antibodies, polyclonal antibodies, chimeric antibodies, antibody fragments, human antibodies, humanized antibodies, or non-human antibodies (e.g. murine, goat, primate, etc.). The therapeutic antibody may be specific for any tumor-specific or tumor-associated antigen. See, e.g. Scott et al., *Cancer Immunity* 2012, 12:14, which is incorporated herein by reference in its entirety.

In one embodiment, the immunotherapy agent is an anti-cancer antibody. Non-limiting examples include trastuzumab (Herceptin®), bevacizumab (Avastin®), cetuximab (Erbitux®), panitumumab (Vectibix®), ipilimumab (Yervoy®), rituximab (Rituxan®), alemtuzumab (Campath®), ofatumumab (Arzerra®), gemtuzumab ozogamicin (Mylotarg®), brentuximab vedotin (Adcetrist®), $^{90}$Y-ibritumomab tiuxetan (Zevalin®), and $^{131}$I-tositumomab (Bexxar®). Additional antibodies are provided in Table 1.

Immune Checkpoint Inhibitors

In one embodiment, the immunotherapy agent is a checkpoint inhibitor. Immune checkpoint proteins are made by some types of immune system cells, such as T cells, and some cancer cells. These proteins, which can prevent T cells from killing cancer cells, are targeted by checkpoint inhibitors. Checkpoint inhibitors increase the T cells' ability to kill the cancer cells. Examples of checkpoint proteins found on T cells or cancer cells include PD-1/PD-L1 and CTLA-4/B7-1/B7-2.

In one embodiment, the checkpoint inhibitor is an antibody to a checkpoint protein, e.g., PD-1, PDL-1, or CTLA-4. Checkpoint inhibitor antibodies include, without limitation, BMS-936559, MPDL3280A, MedI-4736, Lambrolizumab, Alemtuzumab, Atezolizumab, Ipilimumab, Nivolumab, Ofatumumab, Pembrolizumab, and Rituximab.

Cytokines

In one embodiment, the immunotherapy agent is a cytokine. Cytokines stimulate the patient's immune response. Cytokines include interferons and interleukins. In one embodiment, the cytokine is interleukin-2. In one embodiment, the cytokine is interferon-alpha.

Chemotherapy Agents

In one aspect of the present invention, an anti-fugetactic agent is administered in combination with a chemotherapy agent. The chemotherapy agent may be any agent having a therapeutic effect on one or more types of cancer. Many chemotherapy agents are currently known in the art. Types of chemotherapy drugs include, by way of non-limiting example, alkylating agents, antimetabolites, anti-tumor antibiotics, totpoisomerase inhibitors, mitotic inhibitors, corticosteroids, and the like.

Non-limiting examples of chemotherapy drugs are listed in Table 1 and include: nitrogen mustards, such as mechlorethamine (nitrogen mustard), chlorambucil, cyclophosphamide (Cytoxan®), ifosfamide, and melphalan); Nitrosoureas, such as streptozocin, carmustine (BCNU), and lomustine; alkyl sulfonates, such as busulfan; Triazines, such as dacarbazine (DTIC) and temozolomide (Temodar®); ethylenimines, such as thiotepa and altretamine (hexamethylmelamine); platinum drugs, such as cisplatin, carboplatin, and oxalaplatin; 5-fluorouracil (5-FU); 6-mercaptopurine (6-MP); Capecitabine (Xeloda®); Cytarabine (Ara-C®); Floxuridine; Fludarabine; Gemcitabine (Gemzar®); Hydroxyurea; Methotrexate; Pemetrexed (Alimta®); anthracyclines, such as Daunorubicin, Doxorubicin (Adriamycin®). Epirubicin, Idarubicin; Actinomycin-D; Bleomycin; Mitomycin-C; Mitoxantrone; Topotecan; Irinotecan (CPT-11); Etoposide (VP-16); Teniposide; Mitoxantrone; Taxanes: paclitaxel (Taxol®) and docetaxel (Taxotere®); Epothilones: ixabepilone (Ixempra®); Vinca alkaloids: vinblastine (Velban®), vincristine (Oncovin®), and vinorelbine (Navelbine®); Estramustine (Emcyt®); Prednisone; Methylprednisolone (Solumedrol®); Dexamethasone (Decadron®); L-asparaginase; bortezomib (Velcade®). Additional chemotherapy agents are listed, for example, in U.S. Patent Application Pub. No. 2008/0300165, which is incorporated herein by reference in its entirety.

Doses and administration protocols for chemotherapy drugs are well-known in the art. The skilled clinician can readily determine the proper dosing regimen to be used, based on factors including the chemotherapy agent(s) administered, type of cancer being treated, stage of the cancer, age and condition of the patient, patient size, location of the tumor, and the like.

Radiotherapy Agents

In one aspect of the present invention, an anti-fugetactic agent is administered in combination with a radiotherapeutic agent. The radiotherapeutic agent may be any such agent having a therapeutic effect on one or more types of cancer. Many radiotherapeutic agents are currently known in the art. Types of radiotherapeutic drugs include, by way of non-limiting example, X-rays, gamma rays, and charged particles. In one embodiment, the radiotherapeutic agent is delivered by a machine outside of the body (external-beam radiation therapy). In a preferred embodiment, the radiotherapeutic agent is placed in the body near the tumor/cancer cells (brachytherapy) or is a systemic radiation therapy.

External-beam radiation therapy may be administered by any means. Non-limiting examples of external-beam radiation therapy include linear accelerator-administered radiation therapy, 3-dimensional conformal radiation therapy (3D-CRT), intensity-modulated radiation therapy (IMRT), image-guided radiation therapy (IGRT), tomotherapy, stereotactic radiosurgery, photon therapy, stereotactic body radiation therapy, proton beam therapy, and electron beam therapy.

Internal radiation therapy (brachytherapy) may be by any technique or agent. Non-limiting examples of internal radiation therapy include any radioactive agents that can be placed proximal to or within the tumor, such as Radium-226 (Ra-226), Cobalt-60 (Co-60), Cesium-137 (Cs-137), cesium-131, Iridium-192 (Ir-192), Gold-198 (Au-198), Iodine-125 (1-125), palladium-103, yttrium-90, etc. Such agents may be administered by seeds, needles, or any other route of administration, and my be temporary or permanent.

Systemic radiation therapy may be by any technique or agent. Non-limiting examples of systemic radiation therapy include radioactive iodine, ibritumomab tiuxetan (Zevalin®), tositumomab and iodine I 131 tositumomab (Bexxar®), samarium-153-lexidronam (Quadramet®), strontium-89 chloride (Metastron®), metaiodobenzylguanidine, lutetium-177, yttrium-90, strontium-89, and the like.

In one embodiment, a radiosensitizing agent is also administered to the patient. Radiosensitizing agents increase the damaging effect of radiation on cancer cells.

Doses and administration protocols for radiotherapy agents are well-known in the art. The skilled clinician can readily determine the proper dosing regimen to be used, based on factors including the agent(s) administered, type of cancer being treated, stage of the cancer, location of the tumor, age and condition of the patient, patient size, and the like.

Anti-Cancer Vaccines

In one aspect of the present invention, an anti-fugetactic agent is administered in combination with an anti-cancer vaccine (also called cancer vaccine). Anti-cancer vaccines are vaccines that either treat existing cancer or prevent development of a cancer by stimulating an immune reaction to kill the cancer cells. In a preferred embodiment, the anti-cancer vaccine treats existing cancer.

The anti-cancer vaccine may be any such vaccine having a therapeutic effect on one or more types of cancer. Many anti-cancer vaccines are currently known in the art. Such vaccines include, without limitation, dasiprotimut-T, Sipuleucel-T, talimogene laherparepvec, HSPPC-96 complex (Vitespen), L-BLP25, gp100 melanoma vaccine, and any other vaccine that stimulates an immune response to cancer cells when administered to a patient.

Cancers

Cancers or tumors that can be treated by the compounds and methods described herein include, but are not limited to: biliary tract cancer; brain cancer, including glioblastomas and medulloblastomas; breast cancer (including inflammatory breast cancer); cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors escaping immune recognition include glioma, colon carcinoma, colorectal cancer, lymphoid cell-derived leukemia, choriocarcinoma, and melanoma.

In a preferred embodiment, the tumor is a solid tumor. In one embodiment, the tumor is a leukemia. In an especially preferred embodiment, the tumor has a fugetactic effect, e.g., on immune cells. In one embodiment, the fugetactic effect is mediated by over-expression of CXCL12 by the tumor/tumor cells. In one embodiment, tumor expression of CXCL12 can be evaluated prior to administration of a composition as described herein. For example, a patient having a tumor that is determined to express or over-express CXCL12 will be treated using a method and/or composition as described herein.

In one embodiment, the tumor is a brain tumor. It is contemplated that a brain tumor, e.g., an inoperable brain tumor, can be injected with a composition described herein. In one embodiment, an anti-fugetactic agent is administered directly to a brain tumor via a catheter into a blood vessel within or proximal to the brain tumor. Further discussion of catheter or microcatheter administration is described below.

Systemic Administration

In one embodiment, the compositions or complexes or cells described herein can be provided systemically (i.e. can be provided to the patient by circulation), which is provided to all tissues. The compositions or complexes or cells described herein administered systemically are not constrained to a specific location in the patient, but rather are expressed throughout the patient.

The compositions or complexes or cells described herein can be administered in several different ways, in a convenient manner such as by injection (subcutaneous, intravenous, intramuscular, etc.), oral administration, inhalation, transdermal application, or rectal administration. The compositions or complexes or cells described herein can also be administered parenterally or intraperitoneally. Depending on the route of administration, the compositions or complexes or cells described herein may be coated in a material to protect the them from acids and other natural conditions which may kill or otherwise inactivate them.

In certain embodiments, the compositions or complexes or cells described herein are formulated to be suitable for injectable use. Such compositions or complexes or cells described herein can include sterile aqueous solutions (where water soluble) or dispersions and sterile powders for the extemporaneous preparation of sterile injectable solutions or dispersion. Preferably, the compositions or complexes or cells described herein are sterile and fluid to the extent possible. The compositions or complexes or cells described herein will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating one or more compositions or complexes or cells described herein, together or separately with additional immune response stimulating agents or immunosupressants, in the required amount in an appropriate solvent with one or a combination of ingredients enumerated above, as required, followed by filtered sterilization. Generally, dispersions are prepared by incorporating the cells or compositions into a sterile vehicle which contains a basic dispersion medium and the required other ingredients from those enumerated above. In the case of sterile powders for the preparation of sterile injectable solutions, some methods of preparation are vacuum drying and freeze-drying which yields a powder of the active ingredient plus any additional desired ingredient from a previously sterile-filtered solution thereof.

It is advantageous to formulate parenteral compositions in dosage unit form for ease of administration and uniformity of dosage. Dosage unit form as used herein refers to physically discrete units suited as unitary dosages for the treated patients; each unit containing a predetermined quantity of cells, composition or complexes calculated to produce the desired therapeutic effect in association with the required pharmaceutical carrier. The specification for the dosage unit forms of the invention are dictated by and directly dependent on (a) the unique characteristics of the cells, complexes or compositions and the particular therapeutic effect to be achieved, and (b) the limitations inherent in the art of compounding such an agent for the treatment of sensitivity in individuals.

The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in assay preparations of target cells. Exact dosages are determined in conjunction with standard dose-response studies. It will be understood that the amount of the cells, complexes or composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

The toxicity and therapeutic efficacy of the compositions or complexes or cells described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compositions or complexes or cells that exhibit toxic side effects may be used, care should be taken to design a delivery system that targets such compositions or complexes or cells described herein to the site of affected tissue in order to minimize potential damage to uninfected cells and, thereby, reduce side effects.

In one embodiment, a therapeutically effective amount of the compositions or complexes or cells described herein is administered to a patient. The optimal dose of the compositions or complexes or cells described herein given may even vary in the same patient depending upon the time at which it is administered.

The skilled artisan will appreciate that certain factors may influence the dosage required to effectively treat a patient, including but not limited to the severity of the disease or disorder, previous treatments, the general health and/or age of the patient, and other diseases present. Moreover, treatment of a patient with a therapeutically effective amount of the compositions or complexes or cells described herein can include a single treatment or, preferably, can include a series of treatments. It will also be appreciated that the effective dosage of cells, complexes or compositions produced by the cell, composition or complex used for treatment may increase or decrease over the course of a particular treatment. Changes in dosage may result from the results of assays designed to monitor tumor status as is well known in the art.

Actual methods for preparing parenterally administrable compositions or complexes or cells are known or apparent to those skilled in the art and are described in more detail in, for example, Remington's Pharmaceutical Science, 15th ed., Mack Publishing Company, Easton, Pa. (1980), which is incorporated herein by reference.

The compositions or complexes or cells described herein can be administered for prophylactic and/or therapeutic treatments. In therapeutic application, compositions can be administered to a patient already suffering from a disease, in an amount sufficient to reduce or at least temporarily limit tumor growth and related complications. An amount adequate to accomplish this is defined as a "therapeutically effective dose."

Amounts effective for this use will depend upon the clinical situation and the general state of the patient's own immune system. For example, doses for preventing transplant rejection may be lower than those given if the patient presents with clinical symptoms of rejection. Single or multiple administrations of the compositions can be carried out with dose levels and pattern being selected by the treating physician. In any event, the pharmaceutical formulations should provide a quantity of the compositions or complexes or cells described herein sufficient to effectively treat the patient.

Administration at the Site of Tumor

In some embodiments, the compositions or complexes or cells described herein can be provided at, e.g. within or contacting the tumor tissue, or proximal to the location of a tumor. By "proximal to" is meant within an effective distance of the tumor cell, such that the compositions or complexes or cells described herein will reach the tumor tissue directly. The subject methods of providing or creating the cells, complexes or compositions at the tumor site thus provide the compositions or complexes or cells described herein locally to the tumor, while minimizing exposure of compositions or complexes or cells described herein to surrounding non-tumor cells. Without being limited to a specific mode of activity, direct administration of the compositions or complexes or cells described herein to the tumor provides a direct and sustained benefit to the tumor, while reducing autoimmune and immunosuppressive side effects that can be observed in systemic administration.

Methods of administering cells or compositions directly to tumors have been accomplished in other contexts. For example, cells have been administered to a tumor site by injection Rodriguez-Madoz et al., Molecular Therapy (2005) 12, 153-163, incorporated by reference herein in its entirety.

Administration at a Lymph Node Near a Tumor

In still other embodiments, compositions or complexes or cells described herein can be administered directly, or proximal to, the lymph nodes near the tumor. The cells, compositions or complexes can be administered to the lymph nodes by any means disclosed herein.

Dose and Administration

The compositions, as described herein, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result.

The agents described herein may be administered by any appropriate method. Dosage, treatment protocol, and routes of administration for anti-cancer agents, including chemotherapeutic agents, radiotherapeutic agents, and anti-cancer vaccines, as well as immunotherapy agents are known in the art and/or within the ability of a skilled clinician to determine, based on the type of treatment, type of cancer, etc.

Generally, the dose of the anti-fugetactic agent of the present invention is from about 5 mg/kg body weight per day to about 50 mg/kg per day, inclusive of all values and ranges therebetween, including endpoints. In one embodiment, the dose is from about 10 mg kg to about 50 mg/kg per day. In one embodiment, the dose is from about 10 mg/kg to about 40 mg/kg per day. In one embodiment, the dose is from about 10 mg/kg to about 30 mg/kg per day. In a preferred embodiment, the dose is from about 10 mg/kg to about 20 mg/kg per day. In one embodiment, the dose does not exceed about 50 mg per day.

In one embodiment, the dose of the anti-fugetactic agent is from about 70 mg/kg per week to about 350 mg/kg per week, inclusive of all values and ranges therebetween, including endpoints. In one embodiment, the dose of the anti-fugetactic agent is about 70 mg/kg per week. In one embodiment, the dose of the anti-fugetactic agent is about 80 mg/kg per week. In one embodiment, the dose of the anti-fugetactic agent is about 90 mg/kg per week. In one embodiment, the dose of the anti-fugetactic agent is about 100 mg/kg per week. In one embodiment, the dose of the anti-fugetactic agent is about 110 mg/kg per week. In one embodiment, the dose of the anti-fugetactic agent is about 120 mg/kg per week. In one embodiment, the dose of the anti-fugetactic agent is about 130 mg/kg per week. In one embodiment, the dose of the anti-fugetactic agent is about 140 mg/kg per week. In one embodiment, the dose of the anti-fugetactic agent is about 150 mg/kg per week. In one embodiment, the dose of the anti-fugetactic agent is about 160 mg/kg per week. In one embodiment, the dose of the anti-fugetactic agent is about 170 mg/kg per week. In one embodiment, the dose of the anti-fugetactic agent is about 180 mg/kg per week. In one embodiment, the dose of the anti-fugetactic agent is about 190 mg/kg per week. In one embodiment, the dose of the anti-fugetactic agent is about 200 mg/kg per week. In one embodiment, the dose of the anti-fugetactic agent is about 210 mg/kg per week. In one embodiment, the dose of the anti-fugetactic agent is about 220 mg/kg per week. In one embodiment, the dose of the anti-fugetactic agent is about 230 mg/kg per week. In one embodiment, the dose of the anti-fugetactic agent is about 240 mg/kg per week. In one embodiment, the dose of the anti-fugetactic agent is about 250 mg/kg per week. In one embodiment, the dose of the anti-fugetactic agent is about 260 mg/kg per week. In one embodiment, the dose of the anti-fugetactic agent is about 270 mg/kg per week. In one embodiment, the dose of the anti-fugetactic agent is about 280 mg/kg per week. In one embodiment, the dose of the anti-fugetactic agent is about 290 mg/kg per week. In one embodiment, the dose of the anti-fugetactic agent is about 300 mg/kg per week. In one embodiment, the dose of the anti-fugetactic agent is about 310 mg/kg per week. In one embodiment, the dose of the anti-fugetactic agent is about 320 mg/kg per week. In one embodiment, the dose of the anti-fugetactic agent is about 330 mg/kg per week. In one embodiment, the dose of the anti-fugetactic agent is about 340 mg/kg per week. In one embodiment, the dose of the anti-fugetactic agent is about 350 mg/kg per week.

In one aspect of the invention, administration of the antibody-anti-fugetactic agent complex is pulsatile. In one embodiment, an amount of antibody-anti-fugetactic agent complex is administered every 1 hour to every 24 hours, for example every 1 hour, 2 hours, 3 hours, 4 hours, 5 hours, 6 hours, 7 hours, 8 hours, 9 hours, 10 hours, 11 hours, 12 hours, 13 hours, 14 hours 15 hours, 16 hours, 17 hours, 18 hours, 19 hours, 20 hours, 21 hours, 22 hours, 23 hours, or 24 hours. In one embodiment, an amount of antibody-anti-fugetactic agent complex is administered every 1 day, 2 days, 3 days, 4 days, 5 days, 6 days, 7 days, 8 days, 9 days, or 10 days.

In one aspect of the invention, doses of the antibody-anti-fugetactic agent complex are administered in a pulsatile manner for a period of time sufficient to have an anti-fugetactic effect (e.g. to attenuate the fugetactic effect of the tumor cell). In one embodiment, the period of time is between about 1 day and about 10 days. For example, the period of time may be 1 day, 2 days, 3 day s, 4 days, 5 days, 6 days, 7 days, 8 days, 9 days, or 10 days.

In one aspect of the invention, at least one anti-cancer agent is administered. In one embodiment, the antibody-anti-fugetactic agent complex and the anti-cancer agent are administered sequentially. That is, the antibody-anti-fugetactic agent complex may be administered for a period of time sufficient to have an anti-fugetactic effect, and the anti-cancer agent is subsequently administered. In one embodiment, the anti-cancer agent is administered for a period of time sufficient to treat the tumor (e.g., reduce the size of the tumor), and the anti-fugetactic agent is subsequently administered. In one embodiment, the antibody-anti-fugetactic agent complex and the anti-cancer agent are administered at the same time or approximately the same time.

In one aspect of the invention, the anti-cancer agent is administered after the period of time of administration of antibody-anti-fugetactic agent complex. In one embodiment, the anti-cancer agent is administered during a period of time wherein the fugetactic effect of the cancer cells/tumor is attenuated by the antibody-anti-fugetactic agent complex. The length of time and modes of administration of the anti-cancer agent will vary, depending on the anti-cancer agent used, type of tumor being treated, condition of the patient, and the like. Determination of such parameters is within the capability of the skilled clinician.

In one embodiment, administration of the antibody-anti-fugetactic agent complex and the anti-cancer agent is alternated. In a preferred embodiment, administration of the antibody-anti-fugetactic agent and the anti-cancer agent is alternated until the condition of the patient improves. Improvement includes, without limitation, reduction in size of the tumor and/or metastases thereof, elimination of the tumor and/or metastases thereof, remission of the cancer, and/or attenuation of at least one symptom of the cancer.

A variety of administration routes are available. The methods of the invention, generally speaking may be practiced using any mode of administration that is medically acceptable, meaning any mode that produces effective levels of the active compounds without causing clinically unacceptable adverse effects.

Modes of administration include oral, rectal, topical, nasal, interdermal, or parenteral routes. The term "parenteral" includes subcutaneous, intravenous, intramuscular, or infusion. In some embodiments, the compositions and/or complexes described herein are administered intraperitoneally. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent(s). Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed 25 oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In one embodiment, the antibody-anti-fugetactic agent complex is administered parenterally. In one embodiment, the antibody-anti-fugetactic agent complex is administered via microcatheter into a blood vessel proximal to a tumor. In one embodiment, the antibody-anti-fugetactic agent complex is administered via microcatheter into a blood vessel within a tumor. In one embodiment, the antibody-anti-fugetactic agent complex is administered subcutaneously. In one embodiment, the antibody-anti-fugetactic agent complex is administered intradermally.

Other delivery systems can include time-release, delayed release, or sustained release delivery systems. Such systems can avoid repeated administrations of the antibody-anti-fugetactic agent complex, increasing convenience to the subject and the physician. Many types of release delivery systems are available and known to those of ordinary skill in the art. They include polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like.

In one embodiment, the antibody-anti-fugetactic agent is administered in a time-release, delayed release or sustained release delivery system. In one embodiment, the time-release, delayed release or sustained release delivery system comprising the antibody-anti-fugetactic agent complex is inserted directly into the tumor. In one embodiment, the time-release, delayed release or sustained release delivery system comprising the antibody-anti-fugetactic agent complex is implanted in the patient proximal to the tumor. Additional implantable formulations are described, for example, in U.S. Patent App. Pub. No. 2008/0300165, which is incorporated herein by reference in its entirety.

Some embodiments of the invention include pump-based hardware delivery systems, some of which are adapted for implantation. Such implantable pumps include controlled-release microchips. A preferred controlled-release microchip is described in Santini. J T Jr. et al., Nature, 1999, 397:335-338, the contents of which are expressly incorporated herein by reference.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compositions containing antibody-anti-fugetactic agent complexes and optionally the anti-cancer agents of the invention can be administered for therapeutic or prophylactic treatments. In therapeutic applications, compositions are administered to a patient suffering from a disease (e.g., a cancer) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal, e.g. a human, who is suspected of having a significant likelihood of developing cancer.

Compositions comprising antibody-anti-fugetactic agent complexes as described herein can be administered as pharmaceutical compositions and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to adversely affect the biological activity of the antibody. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized SEPHAROSE™ (GE Healthcare Bio-Sciences Ltd.), agarose, cellulose, and the like), polymeric amino acids, amino acid copolymers, and lipid aggregates (such as oil droplets or liposomes).

Pharmaceutical compositions may be injectable compositions. Injectable compositions include solutions, suspensions, dispersions, and the like. Injectable solutions, suspensions, dispersions, and the like may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid.

Injectable compositions may be prepared in water, saline, isotonic saline, phosphate-buffered saline, citrate-buffered saline, and the like and may optionally be mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. Isotonic agents such as sugars, buffers, or sodium chloride may be included. Prolonged absorption of the injectable compositions can be brought about by the inclusion in the composition of agents delaying absorption—for example, aluminum monosterate hydrogels and gelatin. Solubility enhancers may be added.

Methods of Treatment

In one aspect of this invention is provided a method for treating cancer in a patient in need thereof by administration of an antibody-anti-fugetactic agent complex. In one embodiment, the antibody-anti-fugetactic agent complex is administered in combination with an anti-cancer agent.

In one aspect, this invention relates to inhibition of metastasis of a tumor in a patient in need thereof by administration of an antibody-anti-fugetactic agent complex. Without being bound be theory, it is believed that the antibody-anti-fugetactic agent complexes as described herein can mobilize cancer cells out of niches where they are otherwise inaccessible to treatments and/or immune cells, and into the circulation where the cells can be targeted by anti-cancer agents and/or immune cells. Surprisingly, such mobilization does not lead to increased metastasis of the tumor, but rather decreases metastasis.

In one aspect, this invention relates to a method for killing a cancer cell expressing an amount of a chemokine sufficient to produce a fugetactic effect, which method comprises periodically contacting said cell with an effective amount of an antibody-anti-fugetactic agent complex for a sufficient period of time so as to attenuate said fugetactic effect.

In one aspect, this invention relates to a method for killing a cancer cell expressing an amount of a chemokine sufficient to produce a fugetactic effect, which method comprises:
  a) periodically contacting said cell with an effective amount of an antibody-anti-fugetactic agent complex for a sufficient period of time so as to attenuate said fugetactic effect;
  b) optionally contacting said cell with at least one anti-cancer agent; and
  c) optionally repeating a) and b) as necessary to kill said cell.

In one aspect, this invention relates to a method for killing a cancer cell expressing an amount of a chemokine sufficient to produce a fugetactic effect, which method comprises:
- a) periodically contacting said cell with an effective amount of an antibody-anti-fugetactic agent complex for a sufficient period of time so as to inhibit said fugetactic effect;
- b) optionally contacting said cell with an anti-cancer agent:
- c) optionally contacting said cell with at least one immunotherapy agent; and
- d) optionally repeating a), b), and/or c) as necessary to kill said cell.

In one aspect, this invention relates to a method for treating a tumor in a mammal, said tumor expressing an amount of a chemokine sufficient to produce a fugetactic effect, which method comprises:
- a) periodically administering to said mammal an effective amount of an antibody-anti-fugetactic agent complex for a sufficient period of time so as to attenuate said fugetactic effect;
- b) optionally administering to said mammal at least one anti-cancer agent; and
- c) optionally repeating a) and b) as necessary to provide an improvement in the condition of the mammal.

In one embodiment, the anti-cancer agent is administered after the period of time of administration of the antibody-anti-fugetactic agent complex. In one embodiment, the immunotherapy agent is administered during a period of time when the fugetactic effect is attenuated.

In one embodiment, an anti-cancer agent is optionally administered. The anti-cancer agent may be administered subsequent to the antibody-anti-fugetactic agent complex, with the antibody-anti-fugetactic agent complex, prior to the antibody-anti-fugetactic agent complex, or in any combination thereof. In one embodiment, more than one anti-cancer agent is administered. Multiple anti-cancer agents may be administered simultaneously or sequentially.

In one embodiment, the chemokine is CXCL12.

In one embodiment, the cancer cell is a solid tumor cell. In one embodiment, the cancer cell is a leukemia cell. In one embodiment, the anti-cancer agent is administered within about 3 days of completion of contacting the cell with the antibody-anti-fugetactic agent complex. In one embodiment, the anti-cancer agent is administered within about 1 day of completion of contacting the cell with the antibody-anti-fugetactic agent complex. In one embodiment, the anti-cancer agent is administered at approximately the same time as the antibody-anti-fugetactic agent complex. In one embodiment, the anti-cancer agent is administered prior to contacting the cell with the antibody-anti-fugetactic agent complex. In one embodiment, the anti-cancer agent is administered prior to, concurrently with, and/or after contacting the cell with the antibody-anti-fugetactic agent complex.

In one aspect, this invention relates to a method for treating a solid tumor in a mammal which tumor expresses CXCL12 at a concentration sufficient to produce a fugetactic effect, the method comprising administering to said mammal an effective amount of an antibody-anti-fugetactic agent complex for a sufficient period of time so as to inhibit said fugetactic effect. In one embodiment, the cancer cell is a solid tumor cell. In one embodiment, the cancer cell is a leukemia cell.

In one aspect, this invention relates to solid tumor cell expressing a chemokine, which cell has been contacted with an antibody-anti-fugetactic agent complex and optionally an anti-cancer agent. In one embodiment, the chemokine is CXCL12. In one embodiment, the cancer cell is a solid tumor cell. In one embodiment, the cancer cell is a leukemia cell.

In one aspect, this invention relates to a method to locally treat a solid tumor expressing CXCL12 at a concentration sufficient to produce a fugetactic effect in a patient, which method comprises:
- a) identifying an artery or microartery feeding said tumor:
- b) intra-arterially placing a catheter or microcatheter in said artery or microartery proximal to the flow of blood into said tumor wherein said catheter or microcatheter comprising a lumen for delivering a fluid there through and means for delivering said fluid;
- c) periodically administering an effective amount of the antibody-anti-fugetactic agent complex through said catheter or said microcatheter to the artery or microartery feeding said tumor so as to inhibit said fugetactic effect fugetaxis induced by said tumor; and
- d) optionally subsequently administering an effective amount of an anti-cancer agent to the patient.

In one embodiment, the anti-cancer agent is administered using a catheter, a microcatheter, an external radiation source, or is injected or implanted proximal to or within the tumor. In one embodiment, the method further comprises repeating steps a, b, c, and/or d until the patient's condition improves. In one embodiment, the anti-cancer agent is a radiotherapeutic agent, such that the radiotherapeutic agent causes ablation of at least one blood vessel feeding said tumor.

Kit of Parts

This invention further relates to a kit of parts comprising an effective amount of antibody-anti-fugetactic agent complex and optionally at least one anti-cancer agent as described herein. In one embodiment, the kit of parts comprises a first container comprising an antibody-anti-fugetactic agent complex and optionally a second container comprising an anti-cancer agent. In one embodiment, the kit of parts further comprises instructions in a readable medium for dosing and/or administration of the anti-fugetactic agent and/or anti-cancer agent.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

EXAMPLES

The following examples are for illustrative purposes only and should not be interpreted as limitations of the claimed invention. There are a variety of alternative techniques and procedures available to those of skill in the art, which would similarly permit one to successfully perform the intended invention.

Example 1

Mice are injected with tumor cells (subcutaneous injection) from a tumor that expresses high levels of CXCL12 and a tumor allowed to develop. Once the tumor has formed, the mice are injected (subcutaneous in the same flank as the tumor) with an AMD3100 and anti-tumor antigen antibody complex or vehicle, once a day for 5 days.

One to three days after the final dose of AMD3100 and anti-tumor antigen antibody complex, mice are injected via intraperitoneal injection with NK cells or T cells or vehicle 18 hours prior to assay of tumor growth. Tumor growth in mice is delayed by NK cells or T cells treatment, but resumes soon after the treatment is discontinued in mice that were not administered AMD3100. It is contemplated that treatment with AMD3100 and anti-tumor antigen antibody complex prior to treatment with NK cells or T cells will have a synergistic effect, such that the co-treatment results in a delay in tumor growth that is longer than NK cells or T cells alone.

Example 2: Determination of the Anti-Fugetactic Versus Fugetactic Amount of AMD3100

Freshly prepared and purified human $CD3^+$ T cells were prepared from healthy donor peripheral blood. 20,000 T cells were loaded into the upper chamber of the Transwell in control, chemotactic or fugetactic settings with AMD3100 at concentrations between 0.1 µM and 10 µM. Migrated cells were counted in the lower chamber and migration quantitated as previously described. Vianello et al. *The Journal of Immunology*, 2006, 176: 2902-2914; Righi et al., *Cancer Res.*; 71(16): 5522-34, each of which is incorporated herein in its entirety.

Figure 2:
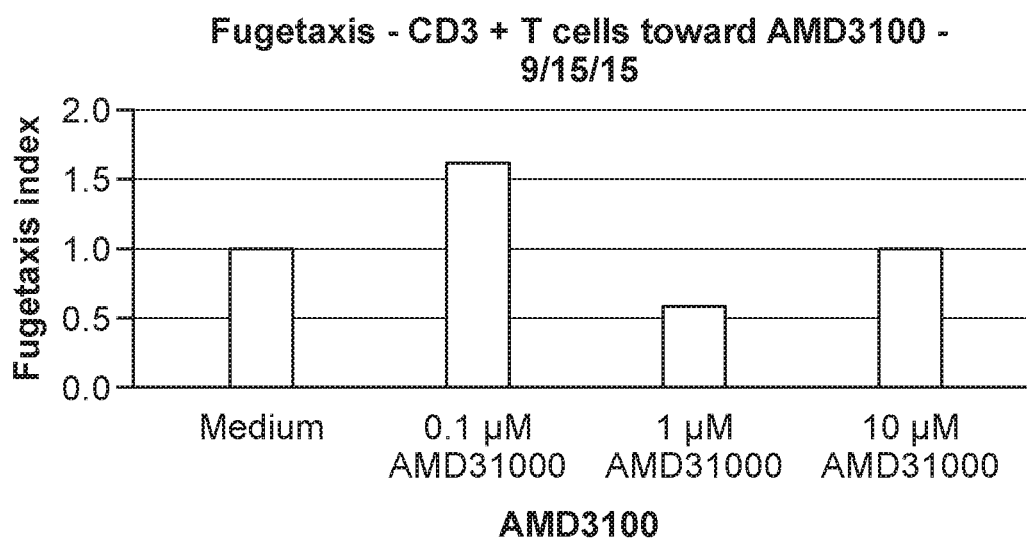
FIG. 2 demonstrates that AMD3100 has a bimodal effect on human T cell fugetaxis. The antifugetactic properties are observed in a specific range.

Clear evidence of binary or bimodal chemotactic (FIG. 1; CI 2.3 at 1 µM) and fugetactic (FIG. 2; CI=1.6 at 0.1 µM) responses of human CD3+ T cells to AMD3100 (where a CI or chemotactic index of 1.0 is the control) was observed. All wells were run in triplicate.

Example 3: Determination of the Local Anti-Fugetactic Amount of AMD3100

For quantitative transmigration assays, purified human CD3' T cells (approximately $2 \times 10^4$ cells) are added to the upper chamber of a Transwell®, insert in each well, to a total volume of 150 µl of Iscove's modified medium. Tumor cells isolated from a mammalian tumor in DMEM containing 0.5% FCS, are added in the lower, upper, or both lower and upper chambers of the Transwell to generate a standard "checkerboard" analysis of cell migration, including measurements of chemotaxis, fugetaxis, and chemokinesis.

To determine the anti-fugetactic concentration of AMD3100, the T cells are incubated with 0.01 µM to 10 mM AMD3100 prior to addition to the chamber.

Cells are harvested from the lower chamber after 3 h, and cell counts are performed using a hemocytometer.

It is expected that T cells that are pre-incubated with a concentration of AMD3100 will exhibit a bimodal effect, with anti-fugetactic effects observed at lower concentrations and fugetactic effects at higher concentrations.

What is claimed is:

1. A kit of parts comprising:
    (a) a first container comprising an antibody-anti-fugetactic agent complex; wherein the complex consists of the antibody and the anti-fugetactic agent selected from the group consisting of AMD3100, KRH-1636, T-20, T-22, T-140, TE-14011, T-14012, TN14003, TAK-779, AK602, SCH-351125, NSC 651016, GF 109230X, tannic acid, and thalidomide, and wherein the antibody has specificity to a tumor antigen selected from the group consisting of EpCAM, CK20, CK30, CD33, CD47, CD52, CD133, CEA gpA33, mucins, TAG-72, CIXPSMA, folate binding protein, GD2 GD3, GM2, VEGH, VEGFR, integrin aV3, integrin a5, and ERBB2; and
    (b) a second container comprising an anti-cancer agent selected from the group consisting of a chemotherapeutic agent, an immunotherapeutic agent, and a radiotherapeutic agent.

2. A composition consisting of an anti-fugetactic agent complexed to an antibody, wherein the anti-fugetactic agent is selected from the group consisting of AMD3100, KRH-1636, T-20, T-22, T-140, TE-14011, T-14012, TN14003, TAK-779, AK602, SCH-351125, NSC 651016, GF 109230X, tannic acid, and thalidomide, and wherein the antibody is specific for a tumor antigen selected from the group consisting of EpCAM, CK20, CK30, CD33, CD47, CD52, CD133, CEA gpA33, mucins, TAG-72, CIXPSMA, folate binding protein, GD2 GD3, GM2, VEGH, VEGFR, integrin aV3, integrin a5, and ERBB2.

3. The composition of claim 2, wherein the anti-fugetactic agent is AMD3100.

4. The kit of parts of claim 1, wherein the anti-fugetactic agent is AMD3100.

5. The composition of claim 2, wherein the anti-fugetactic agent and the antibody are complexed by a covalent bond.

6. The composition of claim 2, wherein the anti-fugetactic agent and the antibody are complexed by a non-covalent bond.

7. The composition of claim 2, wherein the anti-fugetactic agent and the antibody are complexed with albumin.

8. The composition of claim 2, wherein the anti-fugetactic agent and the antibody are complexed with a liposome.

9. The composition of claim 2, wherein the antibody is conjected to an effector moiety, wherein the effector moiety is a cytotoxic agent or anti-cancer agent.

10. The composition of claim 9, wherein the cytotoxic agent is selected from the group consisting of a diphtheria A chain, an exotoxin A chain, a ricin A chain, an abrin A chain, curcin, crotin, phenomycin, enomycin, and auristatin.

11. The kit of parts of claim 1, wherein the anti-fugetactic agent is TAK-779, AK602, or SCH-351125.

12. The kit of parts of claim 1, wherein the anti-fugetactic agent is tannic acid or NSC 651016.

13. The kit of parts of claim 1, wherein the anti-fugetactic agent is thalidomide or GF 109230X.

14. The composition of claim 2, wherein the anti-fugetactic agent is TAK-779, AK602, or SCH-351125.

15. The composition of claim 2, wherein the anti-fugetactic agent is tannic acid or NSC 651016.

16. The composition of claim 2, wherein the anti-fugetactic agent is thalidomide or GF 109230X.

* * * * *

UNITED STATES PATENT AND TRADEMARK OFFICE
CERTIFICATE OF CORRECTION

PATENT NO. : 11,890,348 B2
APPLICATION NO. : 15/760772
DATED : February 6, 2024
INVENTOR(S) : Mark C. Poznansky Page 1 of 1

It is certified that error appears in the above-identified patent and that said Letters Patent is hereby corrected as shown below:

In the Claims

In Column 46, Line 12 (approx.), Claim 1, delete "GD2 GD3," and insert -- GD2, GD3, --

In Column 46, Line 28 (approx.), Claim 2, delete "GD2 GD3," and insert -- GD2, GD3, --

In Column 46, Line 49 (approx.), Claim 10, delete "enomycin," and insert -- neomycin, --

Signed and Sealed this
First Day of October, 2024

Katherine Kelly Vidal
Director of the United States Patent and Trademark Office